(12) United States Patent
Werner et al.

(10) Patent No.: US 7,718,848 B2
(45) Date of Patent: May 18, 2010

(54) SAFE PRODUCTION OF A PRODUCT OF INTEREST IN HYBRID SEEDS

(75) Inventors: Stefan Werner, Halle (DE); Romy Kandzia, Halle (DE); Serik Eliby, Halle (DE); Sylvestre Marillonnet, Halle (DE); Victor Klimyuk, Halle (DE); Yuri Gleba, Halle (DE)

(73) Assignee: Icon Genetics GmbH, Munich (DE)

(*) Notice: Subject to any disclaimer, the term of this patent is extended or adjusted under 35 U.S.C. 154(b) by 738 days.

(21) Appl. No.: 10/559,430

(22) PCT Filed: Jun. 4, 2004

(86) PCT No.: PCT/EP2004/006069

§ 371 (c)(1),
(2), (4) Date: Jan. 17, 2006

(87) PCT Pub. No.: WO2004/108934

PCT Pub. Date: Dec. 16, 2004

(65) Prior Publication Data

US 2006/0272051 A1    Nov. 30, 2006

(30) Foreign Application Priority Data

Jun. 6, 2003  (DE) ................ 103 25 814

(51) Int. Cl.
*C12N 15/82* (2006.01)
*C12N 15/34* (2006.01)
*A01H 1/02* (2006.01)

(52) U.S. Cl. .............. 800/278; 800/260; 800/274; 800/287; 800/288; 435/462; 536/23.72

(58) Field of Classification Search ............. None
See application file for complete search history.

(56) References Cited

U.S. PATENT DOCUMENTS 6,077,992 A * 6/2000 Yadav ............... 800/278
6,632,980 B1 * 10/2003 Yadav et al. ........... 800/278
7,098,383 B2 * 8/2006 Szarka et al. ........... 800/288
7,164,056 B2 * 1/2007 Lyznik et al. ........... 800/278

FOREIGN PATENT DOCUMENTS

| EP | 1048734 A2 | 11/2000 |
| WO | WO 96/04393 A2 | 2/1996 |
| WO | WO 98/37211 A1 | 8/1998 |
| WO | WO 98/44138 A1 | 10/1998 |
| WO | WO 00/70019 | 11/2000 |
| WO | WO 01/85969 | 11/2001 |
| WO | WO 02/088369 A1 | 11/2002 |

OTHER PUBLICATIONS

Stephanopoulos et al. TIBTECH 11: 392-396 (Sep. 1993).*
Colliver et al. Plant Molecular Biology 35: 509-522 (1997).*
Hohn et al. pp. 185-195 In: Plant resistance to viruses (CIBA Foundation Symposium 133), Wiley: Chichester (1987).*
Dawson et al. Virology 172: 285-292 (1989).*
Sengupta-Gopalan et al. Proceedings of the National Academy of Sciences USA 82: 3320-3324 (May 1985).*
Fiedler et al. Bio/Technology 13: 1090-1093 (Oct. 1995).*
Bayley, C. et al., "Exchange of Gene Activity in Transgenic Plants Catalyzed by the Cre-*lox* Site-Specific Recombination System," *Plant Molecular Biology*, 1992, pp. 353-361, vol. 18, Kluwer Academic Publishers, Belgium.

* cited by examiner

*Primary Examiner*—David T Fox
(74) *Attorney, Agent, or Firm*—Alston & Bird LLP

(57) ABSTRACT

A process of the production of a product of interest in an F1 seed obtained by a hybridization of a first and a second transgenic parental plant, said hybridization generating a genetic endowment in said F1 seed for said production by combining in said F1 seed first and second partial genetic endowments of said first and second transgenic parental plants, followed by isolating said product of interest from said F1 seed or a seedling thereof.

10 Claims, 16 Drawing Sheets

SEQUENCE LISTING

<160> NUMBER OF SEQ ID NOS: 26

<210> SEQ ID NO 1
<211> LENGTH: 33
<212> TYPE: DNA
<213> ORGANISM: Artificial Sequence
<220> FEATURE:
<223> OTHER INFORMATION: PCR primer

<400> SEQUENCE: 1
aactgcagtc tagactggcc gtcgttttac aac                33

<210> SEQ ID NO 2

-continued

```
<211> LENGTH: 37
<212> TYPE: DNA
<213> ORGANISM: Artificial Sequence
<220> FEATURE:
<223> OTHER INFORMATION: PCR primer

<400> SEQUENCE: 2
aactgcagaa caattgctcg aggcgtaatc atggtca                              37

<210> SEQ ID NO 3
<211> LENGTH: 40
<212> TYPE: DNA
<213> ORGANISM: Artificial Sequence
<220> FEATURE:
<223> OTHER INFORMATION: PCR primer

<400> SEQUENCE: 3
gggaattcac tagtaaagat ctgccgtcga cttggaattg                           40

<210> SEQ ID NO 4
<211> LENGTH: 28
<212> TYPE: DNA
<213> ORGANISM: Artificial Sequence
<220> FEATURE:
<223> OTHER INFORMATION: PCR primer

<400> SEQUENCE: 4
caatgcatca tggcgcatca cgcttagg                                        28

<210> SEQ ID NO 5
<211> LENGTH: 39
<212> TYPE: DNA
<213> ORGANISM: Artificial Sequence
<220> FEATURE:
<223> OTHER INFORMATION: PCR primer

<400> SEQUENCE: 5
aagctgcaga aggatcctct ggacttacac gtggaatgg                            39

<210> SEQ ID NO 6
<211> LENGTH: 28
<212> TYPE: DNA
<213> ORGANISM: Artificial Sequence
<220> FEATURE:
<223> OTHER INFORMATION: PCR primer

<400> SEQUENCE: 6
cgctcgaggc cgtcgacttg gaattgtc                                        28

<210> SEQ ID NO 7
<211> LENGTH: 25
<212> TYPE: DNA
<213> ORGANISM: Artificial Sequence
<220> FEATURE:
<223> OTHER INFORMATION: PCR primer

<400> SEQUENCE: 7
gaagatctgc aagaggaggt cagca                                           25

<210> SEQ ID NO 8
<211> LENGTH: 33
<212> TYPE: DNA
<213> ORGANISM: Artificial Sequence
<220> FEATURE:
<223> OTHER INFORMATION: PCR primer

<400> SEQUENCE: 8
```
aagctgcaga tctatttcta tgattcgata acc         33

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
gcacgccgaa ggcgacgaag                        20

<210> SEQ ID NO 10
<211> LENGTH: 48
<212> TYPE: DNA
<213> ORGANISM: Artificial Sequence
<220> FEATURE:
<223> OTHER INFORMATION: PCR primer

<400> SEQUENCE: 10
ggatcctaaa ccttcctctt cttcttaggc gccgctacgt cttccgtg    48

<210> SEQ ID NO 11
<211> LENGTH: 21
<212> TYPE: DNA
<213> ORGANISM: Artificial Sequence
<220> FEATURE:
<223> OTHER INFORMATION: PCR primer

<400> SEQUENCE: 11
agaattcaca ccgatgggct c                      21

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
tgaattctgc acactcccac g                      21

<210> SEQ ID NO 13
<211> LENGTH: 31
<212> TYPE: DNA
<213> ORGANISM: Artificial Sequence
<220> FEATURE:
<223> OTHER INFORMATION: PCR primer

<400> SEQUENCE: 13
ttccatggag ttacctcggg agtccttgtt g            31

<210> SEQ ID NO 14
<211> LENGTH: 41
<212> TYPE: DNA
<213> ORGANISM: Artificial Sequence
<220> FEATURE:
<223> OTHER INFORMATION: AttP recombination site

<400> SEQUENCE: 14
ttgcatgcgg ccgcaaaata gtattttatt catctcatgt c    41

<210> SEQ ID NO 15
<211> LENGTH: 51
<212> TYPE: DNA

```
<213> ORGANISM: Artificial Sequence
<220> FEATURE:
<223> OTHER INFORMATION: AttP recombination site

<400> SEQUENCE: 15
gtagtgcccc aactggggta acctttgagt tctctcagtt ggggcgtag a                51

<210> SEQ ID NO 16
<211> LENGTH: 69
<212> TYPE: DNA
<213> ORGANISM: Artificial Sequence
<220> FEATURE:
<223> OTHER INFORMATION: AttB recombination site

<400> SEQUENCE: 16
tcgaagccgc ggtgcgggtg ccagggcgtg cccttgggct cccgggcgc gtactccacc        60 tcacccatc                                                              69

<210> SEQ ID NO 17
<211> LENGTH: 124
<212> TYPE: DNA
<213> ORGANISM: Artificial Sequence
<220> FEATURE:
<223> OTHER INFORMATION: N-terminal barnase part with restriction site

<400> SEQUENCE: 17
gcaatcgatg gcacaggtta tcaacacgtt tgacggggtt gcggattatc ttcagacata      60
tcataagcta cctgataatt acattacaaa atcagaagca caagccctcg gctgggacgt     120
ccgc                                                                  124

<210> SEQ ID NO 18
<211> LENGTH: 245
<212> TYPE: DNA
<213> ORGANISM: Artificial Sequence
<220> FEATURE:
<223> OTHER INFORMATION: C-terminal part of barnase with restriction
      site

<400> SEQUENCE: 18
cgccatgggg tggcatcaaa agggaacctt gcagacgtcg ctccggggaa aagcatcggc      60
ggagacatct tctcaaacag gaaggcaaa ctcccgggca aaagcggacg aacatggcgt     120
gaagcggata ttaactatac atcaggcttc agaaattcag accggattct ttactcaagc    180
gactggctga tttacaaaac aacgaccat tatcagacct ttacaaaaat cagataagga    240
tccgc                                                                 245

<210> SEQ ID NO 19
<211> LENGTH: 43
<212> TYPE: DNA
<213> ORGANISM: Artificial Sequence
<220> FEATURE:
<223> OTHER INFORMATION: PCR primer

<400> SEQUENCE: 19
gtaagcttga cgtcagagag agtggatgca tcagtggaga tag                        43

<210> SEQ ID NO 20
<211> LENGTH: 35
<212> TYPE: DNA
<213> ORGANISM: Artificial Sequence
<220> FEATURE:
<223> OTHER INFORMATION: PCR primer
```

-continued

<400> SEQUENCE: 20
cactgcagct ataattgtaa agaggagctt tctag                    35

<210> SEQ ID NO 21
<211> LENGTH: 45
<212> TYPE: DNA
<213> ORGANISM: Artificial Sequence
<220> FEATURE:
<223> OTHER INFORMATION: PCR primer

<400> SEQUENCE: 21
gtgagctcga tcgattcatg agcccagaaa tagaaaagtt gtctc          45

<210> SEQ ID NO 22
<211> LENGTH: 48
<212> TYPE: DNA
<213> ORGANISM: Artificial Sequence
<220> FEATURE:
<223> OTHER INFORMATION: PCR primer

<400> SEQUENCE: 22
tcaagcttcc atggtcttgc tcttcactgt tatggacaat gatgtcat       48

<210> SEQ ID NO 23
<211> LENGTH: 29
<212> TYPE: DNA
<213> ORGANISM: Artificial Sequence
<220> FEATURE:
<223> OTHER INFORMATION: PCR primer

<400> SEQUENCE: 23
cgcaattggt ggcaagaggt ctaccatct                            29

<210> SEQ ID NO 24
<211> LENGTH: 30
<212> TYPE: DNA
<213> ORGANISM: Artificial Sequence
<220> FEATURE:
<223> OTHER INFORMATION: PCR primer

<400> SEQUENCE: 24
gcgagctctt ctctttctct cactagtatt                           30

<210> SEQ ID NO 25
<211> LENGTH: 30
<212> TYPE: DNA
<213> ORGANISM: Artificial Sequence
<220> FEATURE:
<223> OTHER INFORMATION: PCR primer

<400> SEQUENCE: 25
cggaattcca gctcatcaac caaactctgt                           30

<210> SEQ ID NO 26
<211> LENGTH: 31
<212> TYPE: DNA
<213> ORGANISM: Artificial Sequence
<220> FEATURE:
<223> OTHER INFORMATION: PCR primer

<400> SEQUENCE: 26
gcgagctctt tgctctgtgt ctagactatc c                         31

SAFE PRODUCTION OF A PRODUCT OF INTEREST IN HYBRID SEEDS

CROSS-REFERENCE TO RELATED APPLICATIONS

This application is the U.S. National Stage of International Application PCT/EP2004/006069 filed Jun. 4, 2004, which designates the U.S. and was published by the International Bureau in English on Dec. 16, 2004, and which claims the benefit of German Patent Application No. 103 25 814.0 filed Jun. 6, 2003; both of which are hereby incorporated herein in their entirety by reference.

FIELD OF THE INVENTION

The present invention relates to a process of high yield and safe production of a product,of interest in hybrid seeds (F1 seeds). The invention also relates to seeds produced thereby and to a product of interest isolated from said seeds.

BACKGROUND OF THE INVENTION

The major problems of current genetic engineering processes of plants can be summarized as follows:
1. Generally low yield of the product of interest. Examples are pharmaceutical proteins, enzymes, other proteins, polymers, sugars, polysaccharides, etc. Low yield means high purification/downstream processing costs.
2. Genetic contamination due to free crossing of genetically modified plants with non-transgenic varieties or wild relatives as well as presence of "volunteer" plants in the fields following the harvest. Such events easily occur spontaneously because plants are self-replicating organisms or because of human mistakes or deliberate actions.

Both problems are to a great degree flip sides of the same problem: low yield is usually a result of our desire to construct a plant that is a producer which at the same time retains an ability of going through a full development and reproduction cycle. Combining the process of development and reproduction with the process of transgene expression does not give a solution. Inducible (U.S. Pat. Nos. 5,187,287; 5,847,102; Mett et al., 1993, Proc. Natl. Acad. Sci., 90, 4567-4571; Aoyama & Chua, 1997, Plant J., 11, 605-612; McNellis et al., 1998, Plant J., 14, 247-257; U.S. Pat. No. 6,063,985; Caddick et al., 1997, Nature Biotech., 16, 177-180; WO09321334; Weinmann et al., 1994, Plant J., 5, 559-569) or organ-specific transgene expression systems (U.S. Pat. No. 5,955,361; WO09828431; De Jaeger et al., 2002, Nature Biotech., 20, 1265-1268) do also not provide a solution to the problem of genetic contamination and do not provide for high yield of the product of interest. All inducible and tissue-specific promoters used in the systems mentioned above have basal activity, e.g. they are "leaky", which in the course of generations causes transgene silencing, thus inevitably decreasing the yield of the product of interest. Moreover, the yield is not the only problem, as transgenic plants carrying recombinant genes under control of such inducible systems do not fulfill stringent biosafety criteria, for example in the case of production of recombinant biopharmaceuticals.

The use of amplification vectors based on plant viral elements can potentially provide a partial solution to the mentioned problems, especially when such vectors are used for transient expression (U.S. Pat. Nos. 5,491,076; 5,977,438; 5,316,931; 5,589,367; 5,866,785; WO0229068). However, most of the vectors for transient expression experiments were developed for selected plant species, predominantly of the Nicotiana family (U.S. Pat. Nos. 5,466,788; 5,670,353; 5,866,785; WO02088369). The efficiency of viral vectors for the production of recombinant protein/RNA of interest is also determined by their ability for efficient cell-to cell and systemic movement. The latter parameters are species- and variety dependent, thus severely restricting the freedom to choose hosts for transient expression. A potential solution to this problem is the design of transgenic plants carrying the viral vector stably integrated into the chromosomal DNA. The use of viral vectors designed for the expression of foreign sequences in plants via transfection or stable incorporation into the plant chromosomal DNA was described in numerous reviews (Stanley, J., 1993, Curr Opin Genet Dev., 3, 91-96; Schlesinger, S. 1995, Mol Biotechnol., 3, 155-165; Porta, C. & Lomonossoff, G. 2002, Biotechnol. & Genel. Eng. Rev., 19, 245-291; Awram et al., 2002 Adv Virus Res., 58, 81-124). However, attempts to design transgenic plants with an amplicon vector stably integrated into the chromosomal DNA usually faces the problem of transgene silencing, thus turning this approach useless. In the best case, it provides a yield that is slightly higher than that provided by a strong constitutive promoter, as was shown in late 80s by Hayes and colleagues for GUS and NPT genes (Hayes et al., 1989, Nucl. Acids Res., 17, 2391-2403). Since that time there was no significant breakthrough in achieving high yield, biologically safe recombinant protein production in transgenic plants based on viral replicons.

The work of Mallory and colleagues (2002, Nature Biotechnol., 20, 622-625) on amplicons in hybrid plants, whereby said hybrid plants provide for a suppressor of post-transcriptional gene silencing (PTGS), offers a partial solution to the problem. However, this approach did not give a high yield of the product of interest, that is incompatible with normal plant development. Further, biosafety issues were not addressed. Gooding and colleagues (1999, Nucleic Acids Res., 27, 1709-1718) reported replication of geminiviral vectors in isolated wheat embryos in a scientific study. Possible technical applications were not addressed. Further, this method cannot be scaled up and is therefore of no use for technical applications.

It is therefore an object of the invention to provide a novel process of producing a product of interest like a protein of interest in a plant production system, notably in high yield. It is another object of the invention to provide a biologically safe process of producing a product of interest, notably a protein of interest, in a plant production system, whereby distribution in the environment of transgenic genetic material involved in said process is tightly controlled and occurs with low probability. It is a further object of the invenion to provide a process of producing a product of interest like a protein of interest in a plant production system, whereby plant growth and isolation of the product of interest can be decoupled in space and time without loosing yield or quality of said product of interest.

GENERAL DESCRIPTION OF THE INVENTION

These objects are achieved by a process of the production of a product of interest in an F1 seed, comprising: obtaining said F1 seed by a hybridization of a first and a second transgenic parental plant, said hybridization generating a genetic endowment in said F1 seed for said production by combining in said F1 seed first and second partial genetic endowments of said first and second transgenic parental plants. Said product of interest may then be isolated from said F1 seed or a seedling thereof.

The invention further provides a process of the production of a product of interest in an F1 seed obtained by a hybridization of a first and a second transgenic parental plant, said hybridization generating a genetic endowment in said F1 seed for said production by combining in said F1 seed first and second partial genetic endowments of said first and second transgenic parental plants, whereby said product of interest is not expressed in said first or said second parental plant, followed by isolating said product of interest from said F1 seed or a seedling thereof.

The invention further provides a process of the production of a product of interest in an F1 seed obtained by a hybridization of a first and a second transgenic parental plant, said hybridization generating a genetic endowment in said F1 seed for said production by combining in said F1 seed first and second partial genetic endowments of said first and second transgenic parental plants, whereby said product of interest is not expressed in said first or said second parental plant, said product of interest being a protein of interest, followed by isolating said product of interest from said F1 seed or a seedling thereof.

Further, seeds produced or producible by the above processes are provided and the product of interest isolated from said seeds. Preferably, sexual reproduction of a plant grown from said seeds is impaired, more preferably said plant is sexually sterile.

The inventors of the invention have found a process of producing a product of interest in plant seeds (F1 seeds). The genetic endowment required for said process is generated in said seeds by hybridizing parent plants, i.e. none of the parent plants has the complete genetic endowment required for said process. The seeds wherein the product of interest is produced are destroyed when said product is isolated therefrom. Consequently, the process of the invention is of high biological safety, as the genetic endowment required for said process has a very low probability of being distributed in the environment. Additionally, said F1 seeds may be sterile for further improving biological safety, since a plant grown from said seed cannot reproduce. Further, the process of the invention has the surprising advantage that gene silencing is not a problem for the production of said product of interest. This may be due to the short coexistance of the partial genetic endowments of the parental plants in said seeds. Notably, since production of said product of interest does basically not occur in the parental plants, no transgene silencing can be transmitted to said seeds. As transgene silencing hardly occurs, said product of interest can be produced in high yield. It is a further advantage of the invention that plant growth and isolation of the product of interest can be separated in space and time, since the product of interest is usually more stable in seeds than in other plant tissues. This adds flexibility to the overall process of the invention.

Said first and said second transgenic parental plant contains said first and said second partial genetic endowment, respectively. Said partial genetic endowments are preferably transgenic. Said hybridization of said first and said second transgenic parental plant generates said genetic endowment in said F1 seed obtained by said hybridization. Generation of said genetic endowment in said seed triggers production of said product of interest in said seed. Hybridizing means preferably cross-pollination of said first and said second transgenic parental plant. Said hybridization combines said first and said second partial genetic endowment in said F1 seed to endow said F1 seed with said genetic endowment. Both said first and said second genetic endowments are necessary for said production of said product of interest in said seed. Therefore, said product of interest is not expressed in said first or said second parental plant. Minor levels of production of said product of interest may take place in a parental plant e.g. due to leaky expression from said first or said second partial endowment. Such a leaky expression is too weak for an economical production of said product of interest. Preferably, however, no production of said product of interest takes place neither in said first nor in said second parental plant.

Said product of interest produced by said process is preferably a protein of interest, e.g. a pharmaceutical protein. Two, three or more proteins of interest may also be produced in seeds according to the invention. Said protein of interest is preferably a protein that is heterologous to the plant of said seed. Said protein of interest may be an enzyme. If an enzyme is produced in said seed, said product may also be a chemical compound which is produced in said seed inter alia by the action of said enzyme. Two, three or more enzymes may be necessary for the production of said chemical compound. Examples of chemical compounds that may be produced using the invention include vitamins, polymers (e.g. poly hydroxybutyric acid and other biodegradable polyesters), fatty acids, fat, oil, carbohydrates, higher isoprenoids etc. Seeds containing said product of interest may be harvested from a parental plant and said proteins of interest or said chemical compounds may be isolated from said seed according to known procedures. The seeds from which said product of interest is isolated may have germinated. Said product of interest may accumulate in the developing embryo, in the endosperm, in cotyledons or in germinating seeds.

Production of said product or protein of interest by generation of said genetic endowment may be achieved in many different ways. If a protein is to be produced, each partial genetic endowment may provide a part of a coding sequence for said protein, said parts may be combined in said seed e.g. by recombination on DNA level, by RNA trans-splicing on RNA level, or by protein trans-splicing on the protein level. Another general approach is to provide the coding sequence of the protein of interest with the first partial endowment in a form where said protein is not expressible and to provide a genetic component with the second partial endowment that triggers expression of said protein. Expression may e.g. be triggered by providing with the second partial endowment an RNA polymerase that allows transcription of said coding sequence from a heterologous promoter not recognised by polymerases native to said plant, or by providing with said second partial endowment a recombinase that renders said coding sequence expressible e.g. by placing the coding sequence under the control of a promoter. For further increasing control over the production of the product of interest in said seeds, the coding sequence of the recombinase or another enzyme triggering said production may be split into two fragments. One fragment may be provided to said seeds by said first parental plant, the other fragment may be provided to said seeds by said second parental plant. Said two fragments may be expressed under control of two different developmentally regulated promoters and assembled into the active recombinase or enzyme by intein-mediated trans-splicing in said F1 seeds. In this way, the onset of said production of said product of interest may be controlled, e.g. it may be shifted to a late stage of seed development. Details on intein-mediated trans-splicing may be found in PCT/EP03/02986.

In an important embodiment, said genetic endowment comprises a replicating DNA or a replicating RNA generated by said hybridization. Said replicating DNA or said replicating RNA is involved in the production of said product of interest. Preferably, said protein of interest is expressed from said replicating DNA or said replicating RNA. Said replicating DNA may be a replicon, i.e. it may have an origin of replication functional in said seed. Preferably, said replicon is a viral replicon, i.e. it may have components of a DNA virus like a sequence coding for a DNA viral replicase or a protein involved in spreading of the viral replicon from cell to cell. Similarly, said replicating RNA may be an RNA replicon, i.e. it may have an origin of replication functional in said seeds. Preferably, said RNA replicon is a viral replicon, i.e. it may have components of an RNA virus like a sequence coding for a viral RNA-dependent RNA polymerase or a protein involved in spreading of the viral replicon from cell to cell. Most preferably, said DNA viral replicon or said RNA viral replicon may code for said protein of interest.

Said replicating DNA or said replicating RNA may be of plant viral origin. Said replicating DNA may be based on a geminivirus. In the case of a replicating RNA, said replicating RNA is preferably based on a plus-sense single-stranded RNA virus. Preferred plus-sense single-stranded RNA viruses are tobamoviruses. Most preferably, said replicating RNA is based on a Tobacco Mosaic Virus.

Said replicating DNA or said replicating RNA may be generated in said F1 seed from a component of said first partial genetic endowment and a component of said second partial genetic endowment. A DNA replicon may be generated in said seed by hybridizing a first parental plant having integrated in its genome a precursor of said replicon as said first partial genetic endowment with a second parental plant that may contain or code for a component capable of generating (or rendering replicating) said replicon from said precursor. Said component provided with said second parental plant may be an enzyme (like a site-specific recombinase, a flippase or an integrase) capable of generating said replicon by rearranging the precursor of said replicon. Examples for this embodiment are shown in FIGS. 3, 7, and 9.

Said replicating RNA may be generated from a component of said first partial genetic endowment and a component of said second partial genetic endowment by RNA specific recombination. Alternatively, said first partial genetic endowment may comprise a precursor of said replicating RNA. Said precursor may be a DNA copy of said replicating RNA that is integrated into the genome of said first parental plant. Said replicating RNA may then be generated in said seed by the transcription of the DNA copy of said replicating RNA by a component, notably an RNA polymerase, encoded in said second partial genetic endowment. If an RNA polymerase is used as said component, said RNA polymerase should be adapted to the promoter used for transcribing said DNA copy of the replicating RNA.

If said product of interest, notably said protein of interest, is encoded in a first partial genetic endowment and said second partial genetic endowment provides e.g. a regulatory function for said production, said first partial genetic endowment is preferably provided to said hybridization by the female parent plant. More preferably, said female parent plant is male sterile. In this way, biological safety can further be improved, since no pollen from said first (female) transgenic parental plant is distributed in the environment, and pollen from said second (male) parental plant does not code for said product of interest. Similarly, if said genetic endowment comprises a replicating DNA or replicating RNA, said replicating DNA or RNA is preferably provided by the partial genetic endowment of the female parent plant.

The first partial genetic endowment and the second partial genetic endowment are preferably integrated into the respective parental plant such that they can be transmitted to said seed. For this purpose, they are preferably stably integrated into the genomes of the parental plants. Said parental plants may be produced by transforming plants with a vector containing the desired partial genetic endowment according to known methods of plant biotechnology. Said parental plants are preferably made homozygous with respect to the partial genetic endowment. The parental plant lines may be maintained and propagated by selfing.

The seeds of the invention (F1 seeds) may be harvested and used for isolating said product of interest. Therefore, the transgenic material including said genetic endowment contained in said seeds is not distributed in the environment or propagated by transfer to progeny of said seeds. Preferably, sexual reproduction of plants grown from said seeds is impaired, preferably abolished, and more preferably, said F1 seeds are sterile in order to prevent transfer of said transgenic material to progeny of said seeds. In preferred embodiments, sexual reproduction of plants grown from said seeds is impaired or said seeds are sterile due to strong expression of the product of interest or due to strong replication of said replicating DNA or RNA. Alternatively or additionally, development of plants grown from said seeds is blocked by genetic engineering before reaching the reproductive growing stage, which may be achieved by tissue-specific expression of a toxic substance or a toxic protein interfering with normal plant development. Such a toxic protein may be selected from the group consisting of barnase, Shiga protein, plant transcription factors, or enzymes controlling hormonal status of the plant. Preferably, plant development is blocked before the flowering stage, more preferably before the first leaves form.

A toxic protein (like barnase, cf. example 5) may be expressed as protein fragments that generate the funtion of the toxic protein upon protein trans-splicing of said protein fragments to form the functional toxic protein. If said toxic protein is expressed as two fragments, these two fragments may be transcribed under the control of two different promoters, notably two different tissue-specific or two different developmentally active promoters. Formation of the functional toxic protein may then depend on two promoters having different tissue-specificities, i.e. said toxic protein is formed in active form in tissues wherein both promoters are active. This approach allows a much stricter control over expression of the functional toxic protein than can be achieved with a single tissue-specific promoter which will frequently give leaky expression. Moreover, this approach allows to achieve novel expression patterns, e.g. an expression pattern that cannot be achieved with a known tissue-specific promoter; combining different tissue-specific promoters for said two fragments opens up a combinatorial diversity of possible expression patterns.

The process of the invention shows its full potential in large scale applications. Large scale means application with many plants at the same time, e.g. in a green-house. Most preferably, large scale means application on farm fields. In large scale applications, many plants of the first parental plant line and many plants of the second parental plant line are seeded or planted close to each other in order to enable efficient cross-pollination of plants of the first parental plant line with plants of the second parental plant line. In order to prevent self-pollination, known methods of hybrid seed production e.g. using male sterility of either said first or said second parental plant may be combined with the process of the invention. An example of such a method is that described in PCT/EP03/02986.

The priority document DE 103 25 814 of the present patent application is incorporated herein by reference in its entirety.

BRIEF DESCRIPTION OF THE FIGURES

FIG. 1 shows a general scheme of the process of the invention of high yield production of a product of interest in hybrid seeds (said F1 seeds of the invention).

BEST MODES AND DETAILED DESCRIPTION OF THE INVENTION

The authors of this invention have surprisingly found that high rate cell division alone is not sufficient to provide for virus replication in embryos at least of dicotyledonous plants, but depends on the stage of embryo development as well and is usually shifted to the later stages of seed development. Another surprising finding was the ability of virus-based replicon precursors stably incorporated into chromosomal DNA to replicate upon activation in transgenic seeds (said F1 seeds). To the best of our knowledge, there is no prior art describing this phenomenon.

In the process of the invention, plant reproduction and plant-based production of a product of interest are strictly separated, allowing to drastically improve the yield of said product. Utilizing resources normally needed for plant development and reproduction for the production of said product of interest, e.g. by producing said product of interest in seeds, preferably at certain most suitable stages of development or early germination stage, helps to control genetic contamination.

We propose to use a developmental stage, specifically gamete fusion and fertilization, as a genetic switch that converts the seed growth phase into a production phase. We have engineered different components of said genetic endowment into different parental plants. Said components (said partial genetic endowments), while being inactive in the parental plants, generate said genetic endowment after the hybridization process, thus triggering the production of the product of interest. In a preferred embodiment, we use replicating DNA or RNA (amplification processes) for said production, whereby a high-yield production system is created that takes over embryo and/or endosperm production and results in accumulation of the product of interest in a developing seed while preferably making the seed incapable of subsequent sexual reproduction. The product of interest is accumulated and can be isolated from developing seeds, mature seeds, or germinated seeds.

The cornerstones of this invention are the surprising findings that:

(a) viral vectors are capable of replication in plant seed at the later stages of seed development and the early stages of seed germination, but not or hardly during the early stages of seed formation, notably for dicotyledonous plants;

(b) viral vector precursors that are stably integrated into the chromosomal DNA, can be efficiently activated in hybrid seeds upon crossing with a plant providing an activator element.

Activation in seeds of a replicon stably incorporated into chromosomal DNA at the expense of plant development has not been demonstrated before and allows tight control over the process of the invention and prevents leaky replication which might trigger transgene silencing or interfere with seed development at an too early stage.

Figure 1A:
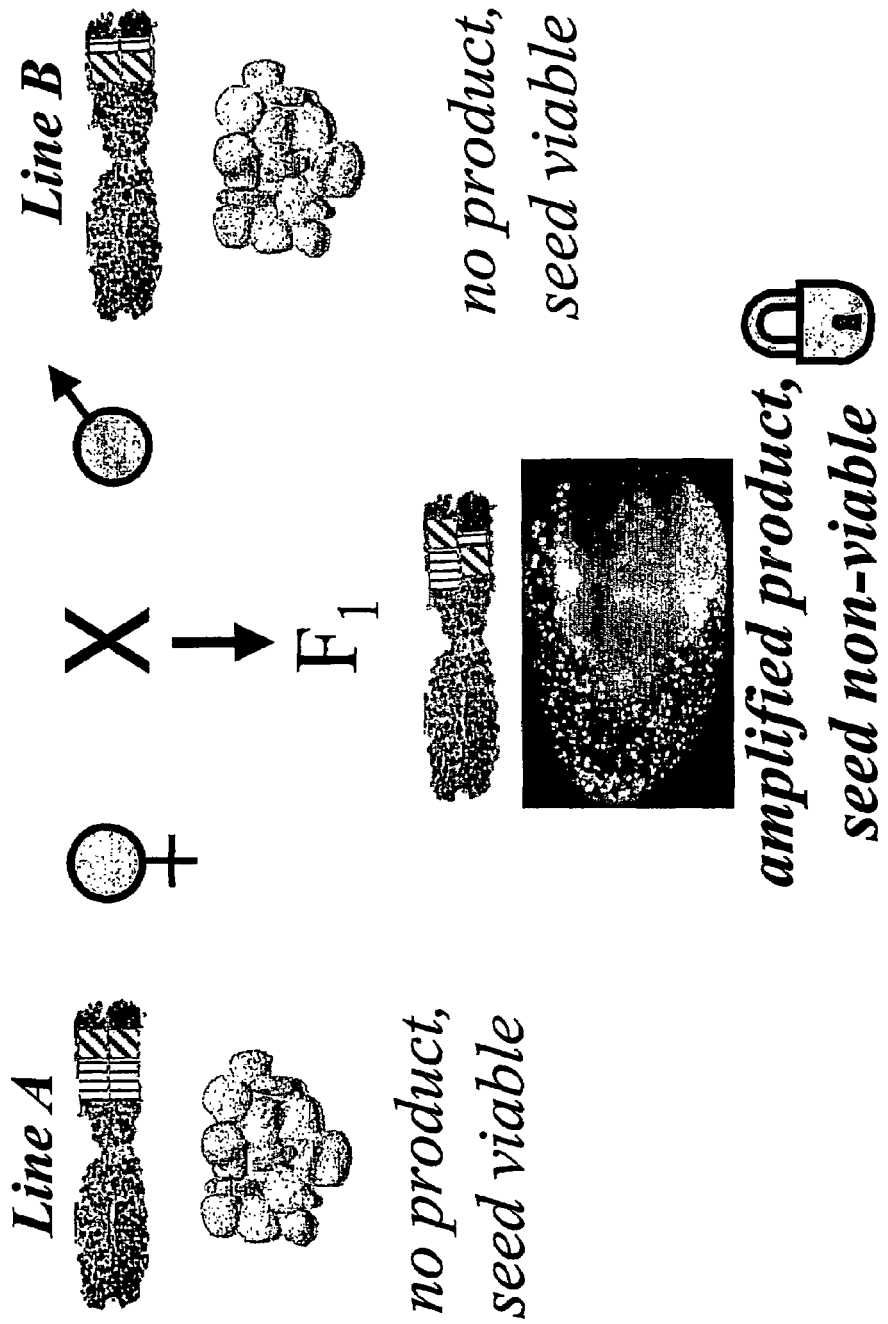
FIG. 1A—General principle of the invention. A first parental plant line A is hybridized with a second parental plant line B to produce F1 seeds. The seeds of both parental lines do not produce the product of interest and these seeds are viable. In F1 seeds, a genetic endowment is generated that allows production of the product of interest, in this case GFP that is observed by its fluorescence (light spots in the photograph). As a result of strong expression of the product of interest optionally in combination with strong replication of a viral vector encoding the product of interest, the F1 seed is non-viable.
Figure 1B:
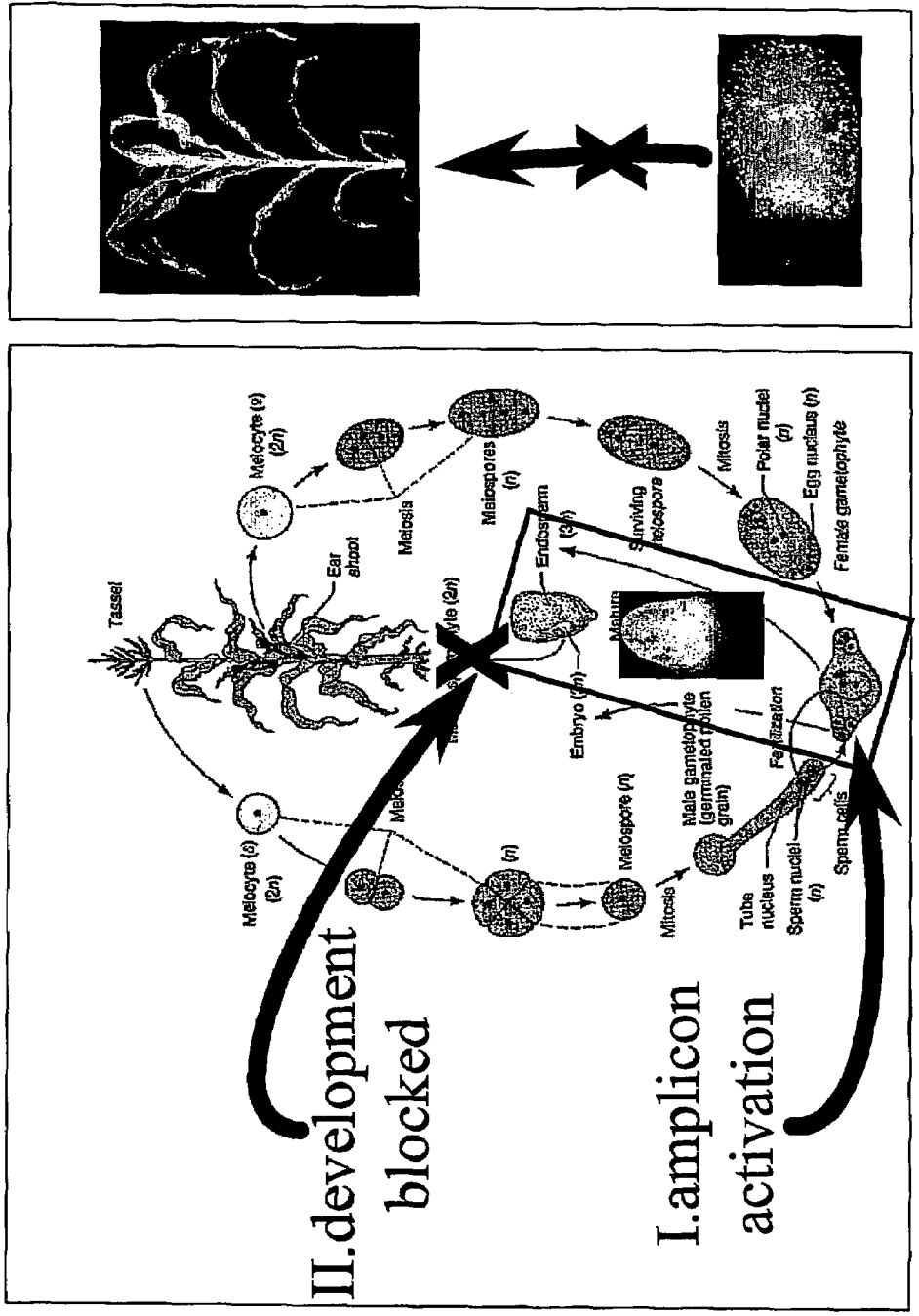
FIG. 1B—Stages of plant development (framed). After hybridization of a sperm cell with a female gametophyte, a seed (F1 seed) is produced that expresses the product of interest (left box). Development of a plant from the F1 seed is blocked. The right box indicates the inability of the F1 seed to grow to a fertile plant.
Figure 2:
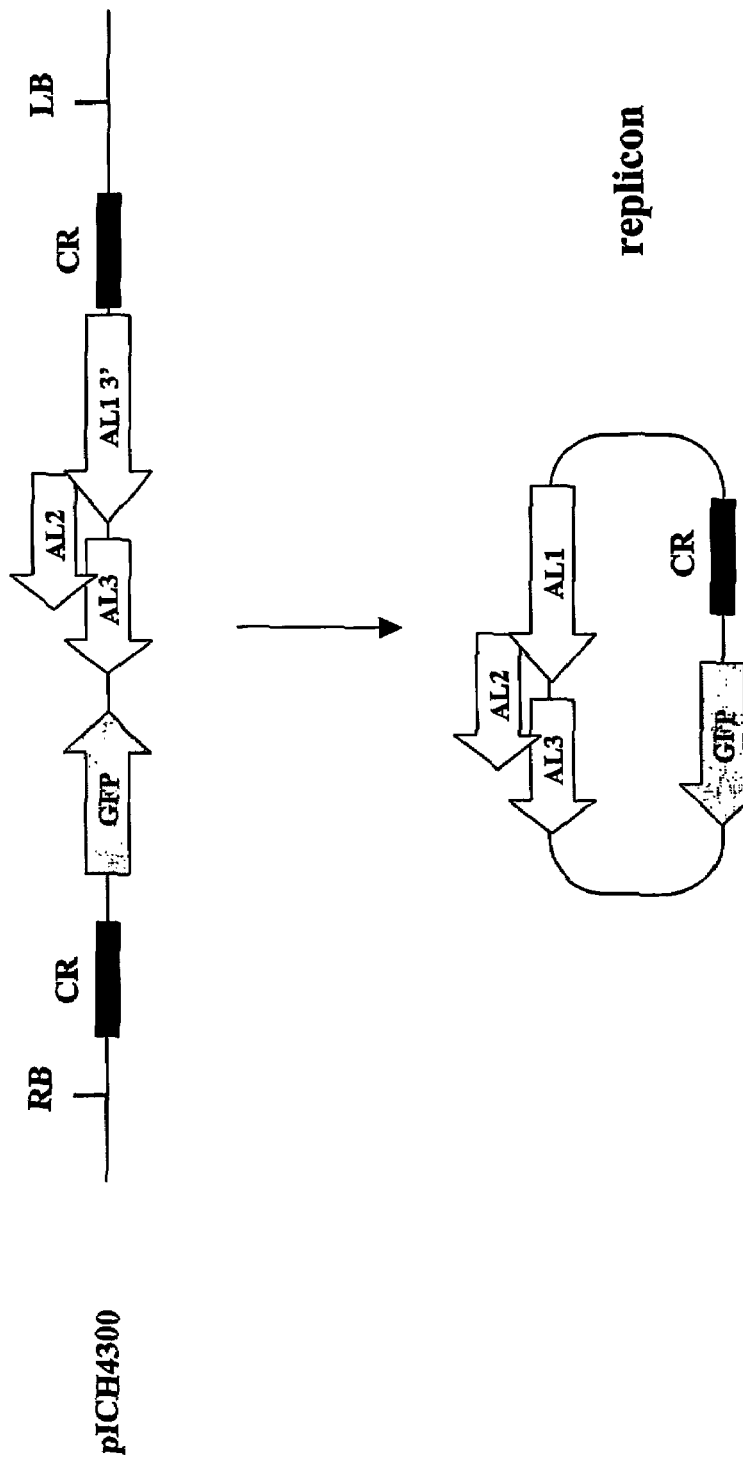
FIG. 2 is a scheme showing the T-DNA region of plasmid pICH4300 and BGMV (Bean Golden Mosaic Virus)-based formation of a DNA replicon in a hybrid seed (cf. example 1).
Figure 3:
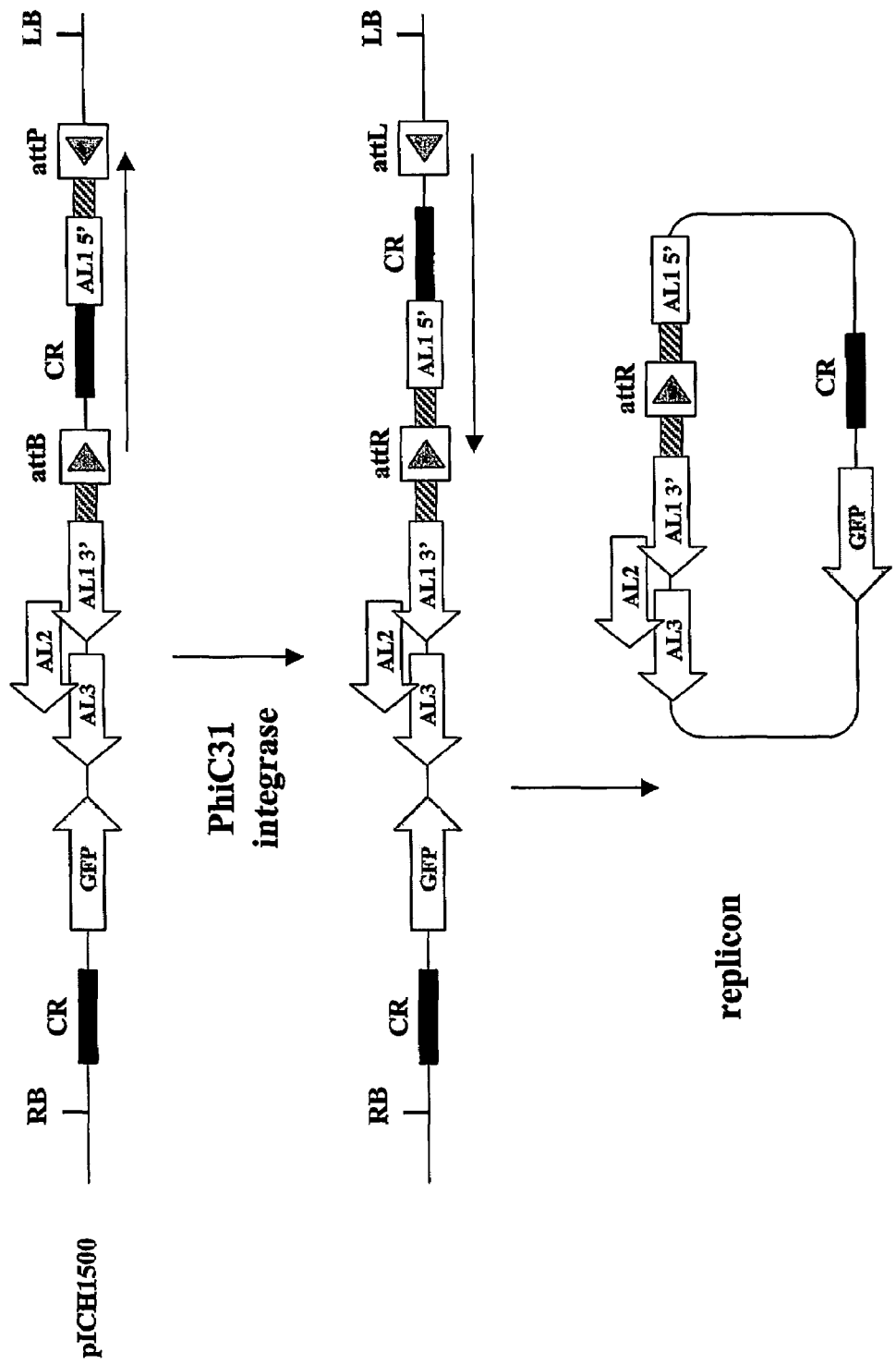
FIG. 3 is a scheme showing the T-DNA region of plasmid pICH1500 and formation of a DNA replicon in the presence of integrase activity (cf. example 1). The genetic elements of pICH1500 may be provided to said seed with said first partial genetic endowment. Integrase PhiC31 may be encoded and provided to said seed with said second partial genetic endowment.
Figure 4:
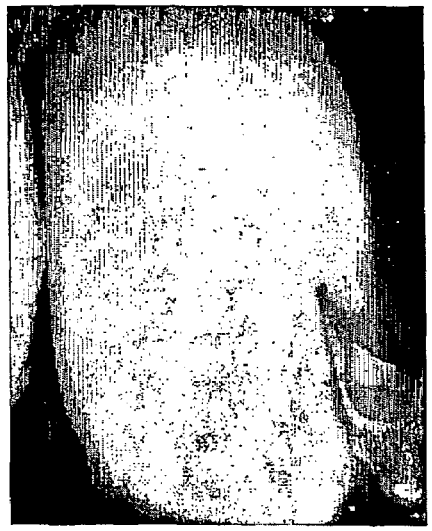
FIG. 4 shows immature embryos of the bean *Phaseolus vulgaris* (A, big picture on the left) and a cotyledon from a germinating seed of the mungbean *Vigna radiata* (B, small pictures on the right) bombarded with plasmid pICH5184. The embryos of beans expresing GFP as the product of interest are encircled.
Figure 4:
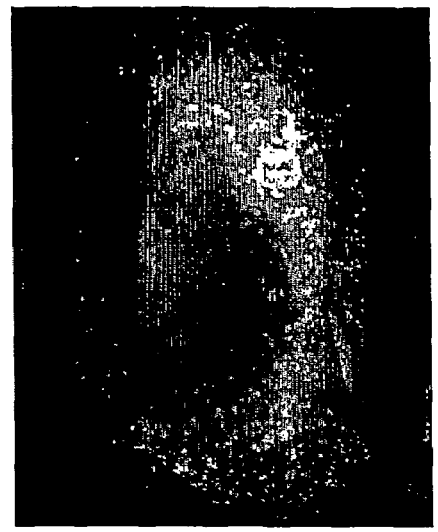
Figure 4:
Figure 5:
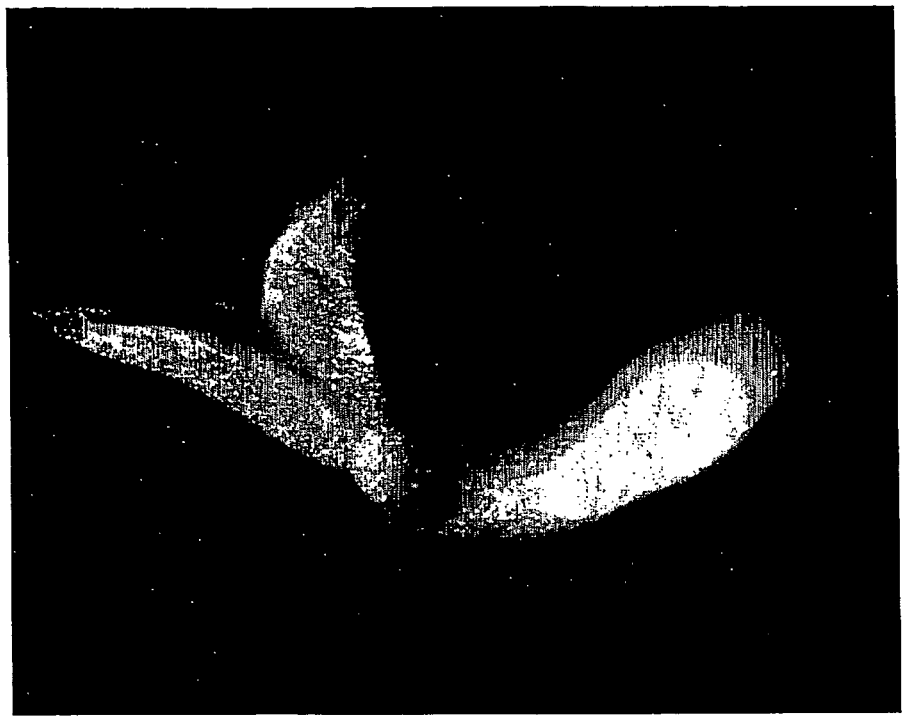
FIG. 5 shows shoots of a germinating seed of the mungbean bombarded with the pICH5184 vector under daylight (left) and under uv-light (right).
Figure 5:
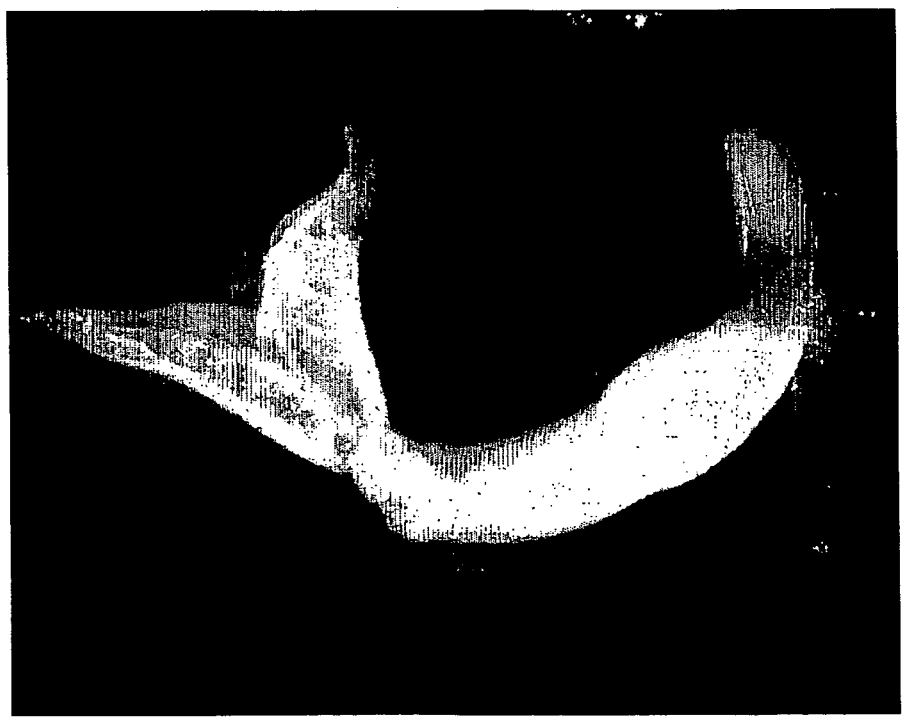
Figure 7:
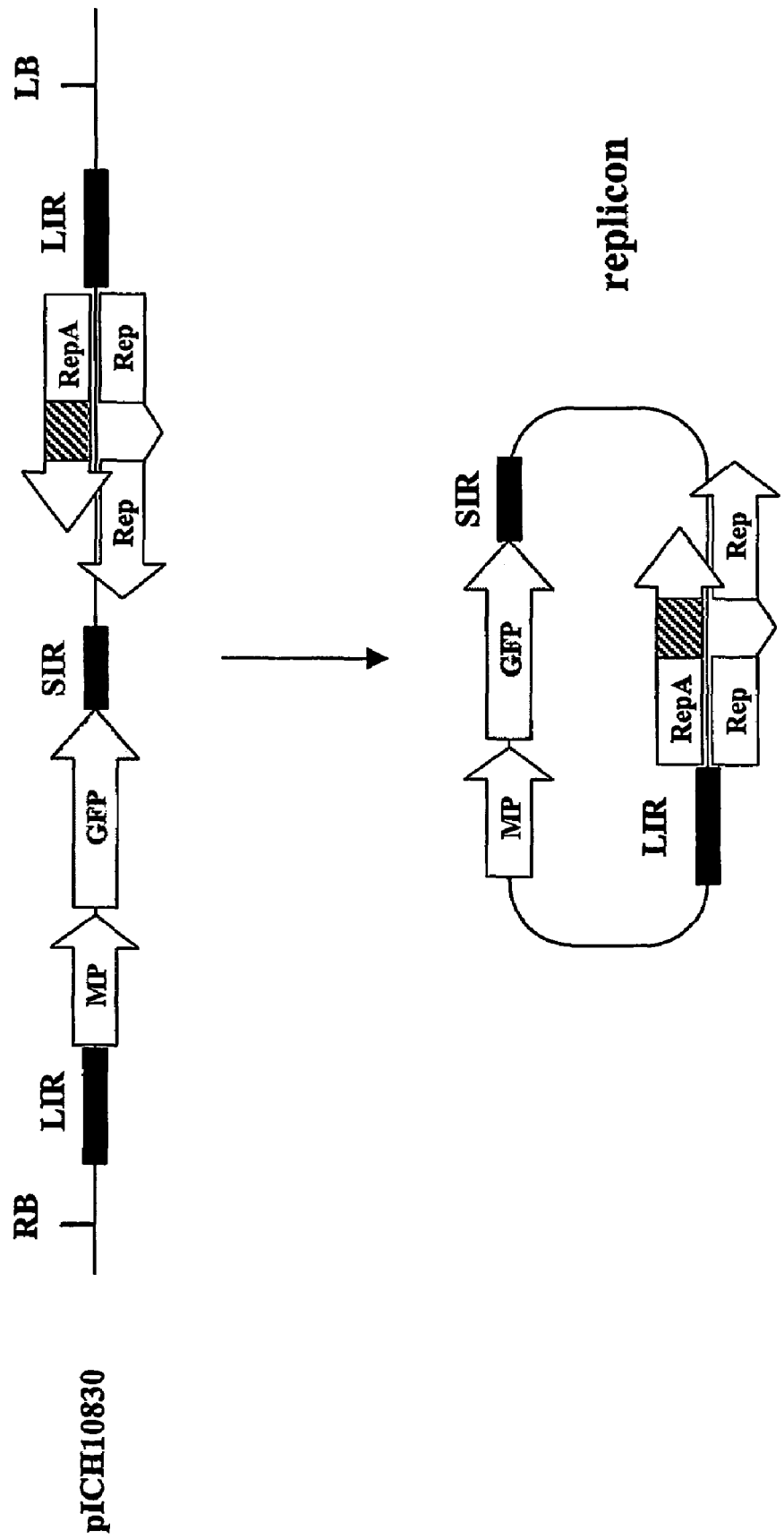
FIG. 7 shows a scheme of the T-DNA region of plasmid pICH10830 and WDV (Wheat Dwarf Virus)-based formation of a DNA replicon (cf. example 2).
Figure 8:
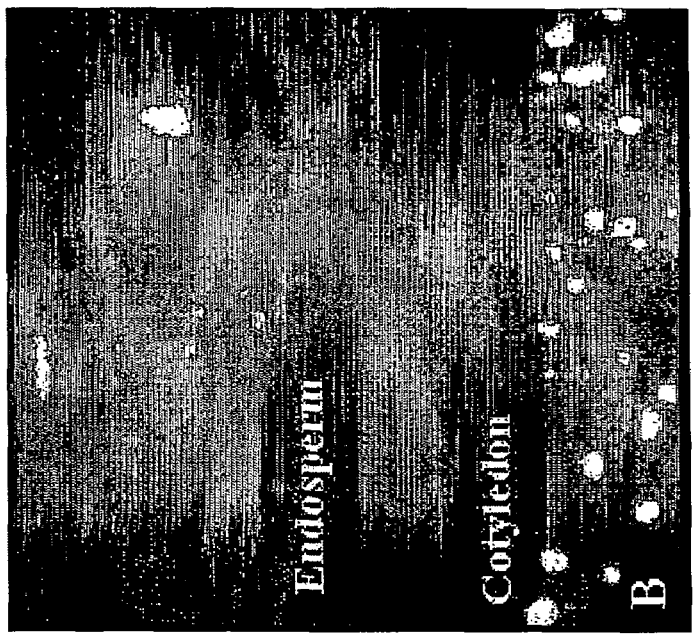
FIG. 8 shows results of bombardment with plasmid pICH10830 containing a wheat dwarf virus (WDV)-GFP expression cassette in wheat embryo (A) and corn seed tissues (B) four days after transformation.
Figure 8:
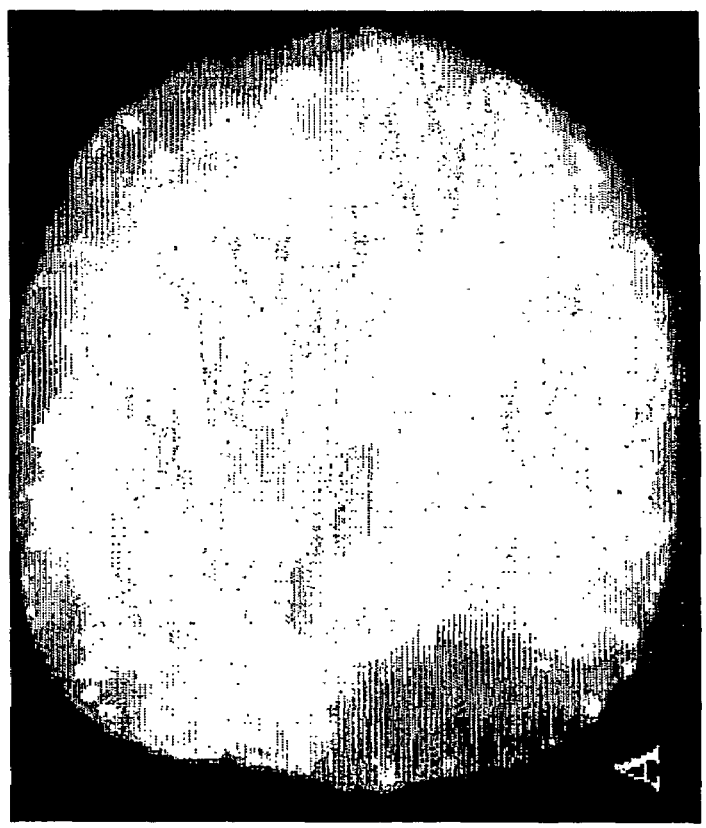

The design of Bean Golden Mosaic Virus (BGMV)-based replicons is described in EXAMPLE 1 and is shown in the FIGS. 2 and 3. The vector pICH4300 carrying GFP (green fluorescent protein) as a reporter gene was used for testing the competence of embryos at different stages of their development for geminiviral replication. The results of these experiments are shown in FIG. 4. It is evident that there is no sign of viral replication (no GFP expression) visible on the surfaces of bombarded young bean embryos, but clear GFP expression was detected in the cells of most advanced embryos (FIG. 4) at their late stages of development. Efficient replication also takes place during seed germination (FIG. 5). Design of Wheat Dwarf Virus (WDV)-based vectors is described in EXAMPLE 2. FIG. 7 shows schematically a WDV vector for transient expression experiments. The results of experiments with wheat and maize seeds are shown in FIG. 8. It is evident that the WDV vector efficiently replicates in wheat and maize embryos, but with lower efficiency in maize endosperm. These data were crucial in establishing the workability of the invention, as leaky replication at undesired (too early) stages of seed development would compromise seed growth and the technical applicability of this approach. It also allows a broader choice of seed-specific promoters for triggering the replication process by site-specific recombination. The activation of the viral vector during early stages of embryo development by recombination-mediated flipping of its part (FIGS. 3 and 9) may bring the replicon precursor to a replication-competent stage, but replication does preferably not occur until the embryo reaches a more advanced ("replication competent") stage of its development.

The choice of the promoter influences the efficiency of this technology. Inducible and tissue-specific promoters can be used to trigger the high yield production in said seed. Inducible promoters can be divided into two categories according to their induction conditions: those induced by abiotic factors (temperature, light, chemical substances) and those that can be induced by biotic factors, for example, pathogen or pest attack. Examples of the first category are inter alia heat-inducible (U.S. Pat. No. 5,187,287) and cold-inducible (U.S. Pat. No. 5,847,102) promoters, a copper-inducible system (Mett et al., 1993, *Proc. Natl. Acad. Sci.,* 90, 4567-4571), steroid-inducible systems (Aoyama & Chua, 1997, *Plant J.,* 11, 605-612; McNellis et al., 1998, *Plant J.,* 14, 247-257; U.S. Pat. No. 6,063,985), an ethanol-inducible system (Caddick et al., 1997, *Nature Biotech.,* 16, 177-180; WO09321334), and a tetracycline-inducible system (Weinmann et al., 1994, *Plant J.,* 5, 559-569). One of the latest developments in the area of chemically inducible systems for plants is a chimaeric promoter that can be switched on by the glucocorticoid dexamethasone and switched off by tetracycline (Bohner et al., 1999, *Plant J.,* 19, 87-95). For a review on chemically inducible systems see: Zuo & Chua, (2000, *Current Opin. Biotechnol.,* 11, 146-151). However, the most suitable promoters for practicing the invention are seed-specific promoters.

There is a broad choice of seed-specific promoters that can be useful for practicing the invention. Such promoters include inter alia the promoter of the pea lectin (PsI1) gene (de Pater et al, 1996, *Plant Mol. Biol.,* 32, 515-523), the promoter of the *Vicia* faba non-storage seed protein gene called USP (Fiedler et al, 1993, *Plant Mol. Biol.,* 22, 669-679), endosperm-specific promoter of the oat globulin gene asglo 5 (Schubert et al., 1994, *Plant Mol. Biol.,* 26, 203-210), the promoter of the maize O2 gene (Gallusci et al., 1994, *Mol. Gen. Genet.,* 15, 391-400), promoters of late embryogenesis abundant genes (lea), specifically AtEm6 providing for the expression throughout the *Arabidopsis* embryo (Vicient et al., 2000, *J. Exp. Botany,* 51, 1211-1220), the promoter of the maize rab17 gene (Busk et al., 1997, *Plant J.,* 11, 1285-1295), beta-phaseolin and beta-conglycinin promoters (Odell et al., 1994, *Plant Physiol.,* 106, 447-458), the promoter of the arcelin-5 gene of *Phaseolus vulgaris* (Gossens et al., 1999, *Plant Physiol,* 120, 1095-1104), the D-hordein gene promoter (Horwath et al., 1999, *Proc. Natl. Acad. Sci. USA,* 97, 1914-1919), the promoter of barley lipoxigenase 1 (Lox1) gene (Rouster et al., 1998, *Plant J.,* 15, 435-440) etc.

In order to preliminarily evaluate the applicability of a chosen promoter to drive the expression of a protein of interest, we have used the GUS reporter gene in transient expression experiments with constructs derived from pIC01 (FIG. 6), where the 34S promoter was replaced with the seed-specific promoter. For driving the expression of integrase PhC31 we have chosen several monocot and dicot seed-specific promoters including the promoter of the USP gene from Vicia faba (Fiedler et al, 1993, *Plant Mol. Biol.,* 22, 669-679), the promoter of the AtEm6 gene (Vicient et al., 2000, *J. Exp. Botany,* 51, 1211-1220), the promoter of maize rab17 gene (Busk et al., 1997, *Plant J.,* 11, 1285-1295) as well as constitutive promoters of *arabidopsis* actin 2 and rice actin 1 genes (constructs pICH14540, pICH14550, pICH14560, pICH10881 and pICH14530 respectively, see FIG. 6). Many other site-specific recombinases can be used in this invention. Examples of such systems include inter alia the Cre-Lox system from bacteriophage P1 (Austin et al., 1981, *Cell,* 25, 729-736), the Flp-Frt system from *Saccharomyces cerevisiae* (Broach et al., 1982, *Cell,* 29, 227-234), the R-RS system from *Zygosaccharomyces rouxii* (Araki et al., 1985, *J. Mol. Biol.,* 182, 191-203).

There is prior art concerning viral replicons in embryos of natural hosts as well as non-host plant species (Wang & Maule, 1994, *Plant Cell,* 6, 777-787; Gooding et al., 1999, *Nucleic Acids Res.,* 27, 1709-1718; Escaler et al., 2000, *Virology,* 267, 318-325; Ugaki et al., 1991, 19, 371-377). It is very likely that the host range can be significantly increased if certain properties of viral replicons determining their host specificity are sacrificed, like cell-to-cell and systemic movement. It is very likely that such viral replicons can efficiently replicate in cells of a broader range of plant species including seed cells, whereby said plant species are not the natural hosts to said viral replicons. In such cases, systemic and cell-to-cell movement of viral replicons may be affected but not the ability to replicate. Actually, viruses belonging to different taxonomic groups can be used for the construction of virus-based vectors according to the principles of the present invention. This is true for both RNA- and DNA-containing viruses, examples for which are given in the following (throughout this document, each type species' name is preceded by the name of the order, family and genus it belongs to. Names of orders, families and genera are in italic script, if they are approved by the ICTV. Taxa names in quotes (and not in italic script) indicate that this taxon does not have an ICTV international approved name. Species (vernacular) names are given in regular script. Viruses with no formal assignment to genus or family are indicated):

DNA Viruses:
  Circular dsDNA Viruses: Family: Caulimoviridae, Genus: *Badnavirus*, Type species: commelina yellow mottle virus, Genus: *Caulimovirus*, Type species: cauliflower mosaic virus, Genus "SbCMV-like viruses", Type species: Soybean chloroticmottle virus, Genus "CsVMV-like viruses", Type species: Cassava vein mosaicvirus, Genus "RTBV-like viruses", Type species: Rice tungro bacilliformvirus, Genus: "Petunia vein clearing-like viruses", Type species: Petunia vein clearing virus;

Circular ssDNA Viruses: Family: Geminiviridae, Genus: *Mastrevirus* (Subgroup I Geminivirus), Type species: maize streak virus, Genus: *Curtovirus* (Subgroup II Geminivirus), Type species: beet curly top virus, Genus: *Begomovirus* (Subgroup III Geminivirus), Type species: bean golden mosaic virus;

RNA Viruses:

ssRNA Viruses: Family: Bromoviridae, Genus: *Alfamovirus*, Type species: alfalfa mosaic virus, Genus: Ilarvirus, Type species: tobacco streak virus, Genus: *Bromovirus*, Type species: brome mosaic virus, Genus: *Cucumovirus*, Type species: cucumber mosaic virus;

Family: Closteroviridae, Genus: *Closterovirus*, Type species: beet yellows virus, Genus: *Crinivirus*, Type species: Lettuce infectious yellows virus, Family: Comoviridae, Genus: *Comovirus*, Type species: cowpea mosaic virus, Genus: *Fabavirus*, Type species: broad bean wilt virus 1, Genus: *Nepovirus*, Type species: tobacco ringspot virus;

Family: Potyviridae, Genus: *Potyvirus*, Type species: potato virus Y, Genus: *Rymovirus*, Type species: ryegrass mosaic virus, Genus: *Bymovirus*, Type species: barley yellow mosaic virus;

Family: Sequiviridae, Genus: *Sequivirus*, Type species: parsnip yellow fleck virus, Genus: *Waikavirus*, Type species: rice tungro spherical virus; Family: Tombusviridae, Genus: *Carmovirus*, Type species: carnation mottle virus, Genus: *Dianthovirus*, Type species: carnation ringspot virus, Genus: *Machlomovirus*, Type species: maize chlorotic mottle virus, Genus: Necrovirus, Type species: tobacco necrosis virus, Genus: *Tombusvirus*, Type species: tomato bushy stunt virus, Unassigned Genera of ssRNA viruses, Genus: *Capillovirus*, Type species: apple stem grooving virus;

Genus: *Carlavirus*, Type species: carnation latent virus; Genus: *Enamovirus*, Type species: pea enation mosaic virus, Genus: *Furovirus*, Type species: soil-borne wheat mosaic virus, Genus: *Hordeivirus*, Type species: barley stripe mosaic virus, Genus: *Idaeovirus*, Type species: raspberry bushy dwarf virus;

Genus: *Luteovirus*, Type species: barley yellow dwarf virus; Genus: *Marafivirus*, Type species: maize rayado fino virus; Genus: *Potexvirus*, Type species: potato virus X; Genus: *Sobemovirus*, Type species: Southern bean mosaic virus, Genus: *Tenuivirus*, Type species: rice stripe virus, Genus: *Tobamovirus*, Type species: tobacco mosaic virus, Genus: *Tobravirus*, Type species: tobacco rattle virus, Genus: *Trichovirus*, Type species: apple chlorotic leaf spot virus; Genus: *Tymovirus*, Type species: turnip yellow mosaic virus; Genus: *Umbravirus*, Type species: carrot mottle virus; Negative ssRNA Viruses: Order: Mononegavirales, Family: Rhabdoviridae, Genus: *Cytorhabdovirus*, Type Species: lettuce necrotic yellows virus, Genus: *Nucleorhabdovirus*, Type species: potato yellow dwarf virus;

Negative ssRNA Viruses: Family: Bunyaviridae, Genus: *Tospovirus*, Type species: tomato spotted wilt virus;

dsRNA Viruses: Family: Partitiviridae, Genus: *Alphacryptovirus*, Type species: white clover cryptic virus 1, Genus: Betacryptovirus, Type species: white clover cryptic virus 2, Family: Reoviridae, Genus: *Fijivirus*, Type species: Fiji disease virus, Genus: *Phytoreovirus*, Type species: wound tumor virus, Genus: *Oryzavirus*, Type species: rice ragged stunt virus;

Unassigned Viruses: Genome ssDNA: Species: banana bunchy top virus, Species: coconut foliar decay virus, Species: subterranean clover stunt virus, Genome: dsDNA, Species: cucumber vein yellowing virus; Genome: dsRNA, Species: tobacco stunt virus, Genome: ssRNA, Species Garlic viruses A,B,C,D, Species grapevine fleck virus, Species maize white line mosaic virus, Species olive latent virus 2, Species: ourmia melon virus, Species Pelargonium zonate spot virus;

Satellites and Viroids: Satellites: ssRNA Satellite Viruses: Subgroup 2 Satellite Viruses, Type species: tobacco necrosis satellite, Satellite RNA, Subgroup 2 B Type mRNA Satellites, Subgroup 3C Type linear RNA Satellites, Subgroup 4 D Type circular RNA Satellites, Viroids, Type species: potato spindle tuber viroid.

Mostly, vectors of plant viral origin are used as plasmids capable of autonomous replication in plants (replicons) for this invention. However the principles necessary for engineering such plasmids using non-viral elements are known. For example, many putative origins of replication from plant cells have been described (Berlani et al., 1988, *Plant Mol. Biol.*, 11, 161-162; Hernandes et al.,1988, *Plant Mol. Biol.*, 10, 413-422; Berlani et al., 1988, *Plant Mol. Biol.*, 11, 173-182; Eckdahl et al., 1989, *Plant Mol. Biol.*, 12, 507-516). It has been shown that the autonomously replicating sequences (ARS elements) from genomes of higher plants have structural and sequence features in common with ARS elements from yeast and higher animals (Eckdahl et al., 1989, *Plant Mol. Biol.*, 12, 507-516). Plant ARS elements are capable of conferring autonomous replicating ability to plasmids in *Saccharomyces cerevisiae*. Studies of maize nuclear DNA sequences capable of promoting autonomous replication of plasmids in yeast showed that they represent two families of highly repeated sequences within the maize genome. Those sequences have a characteristic genomic hybridization pattern. Typically there was only one copy of an ARS-homologous sequence on each 12-15 kb of genomic fragment(Berlani et al., 1988, *Plant Mol. Biol.*, 11:161-162). Another source of replicons of plant origin are plant ribosomal DNA spacer elements that can stimulate the amplification and expression of heterologous genes in plants (Borisjuk et al., 2000, *Nature Biotech.*, 18, 1303-1306). The desired effect of high rate amplification also can be achieved by using strong promoters. Such promoters can provide for high copy number of a transcript of interest, thus giving a net result similar to a replicating vector.

Therefore, a replicon or precursor vector contemplated in this invention is not necessarily derived from a plant virus. Plant DNA viruses provide an easy way of engineering replicons (vectors) that could be especially useful for targeted DNA transformation, but vectors made entirely or partially of elements from plant RNA viruses or even non-plant viruses are possible. Plant virus-based replicons are evidently advantageous. Such replicons, in addition to replication, may provide additional useful functions e.g. for cell to cell and long distance movement. Further, they can frequently be removed more easily from the plant cell a posteriori by using known methods of virus eradication from infected plants.

Figure 9:
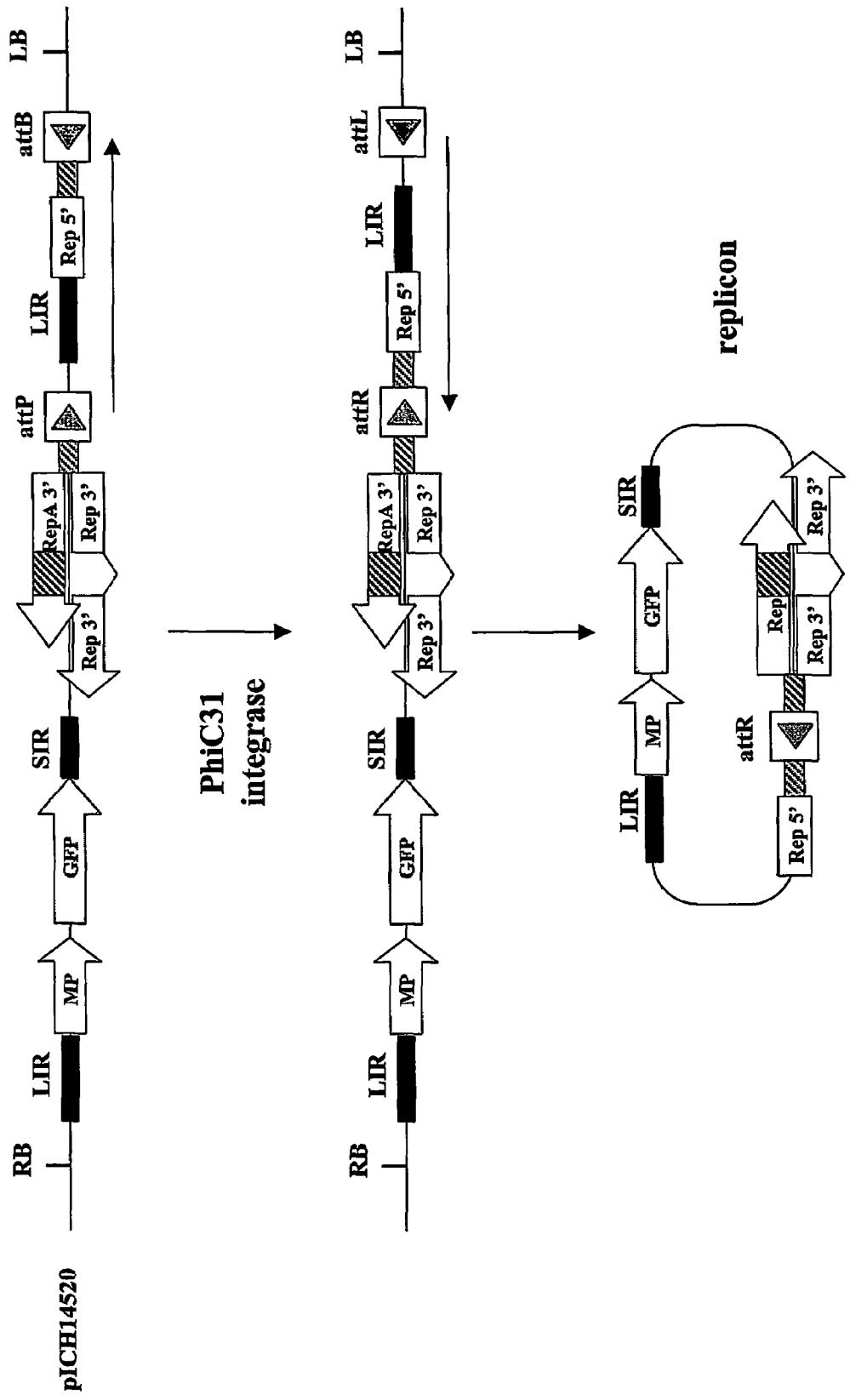
FIG. 9 shows a scheme of the T-DNA region of plasmid pICH14520 and replicon formation in the presence of integrase PhiC31 activity. LIR and SIR are Long and Short Intergenic Regions of wheat dwarf virus; MP—movement protein; Rep—viral replicase; RepA viral replicase A.
Figure 11:
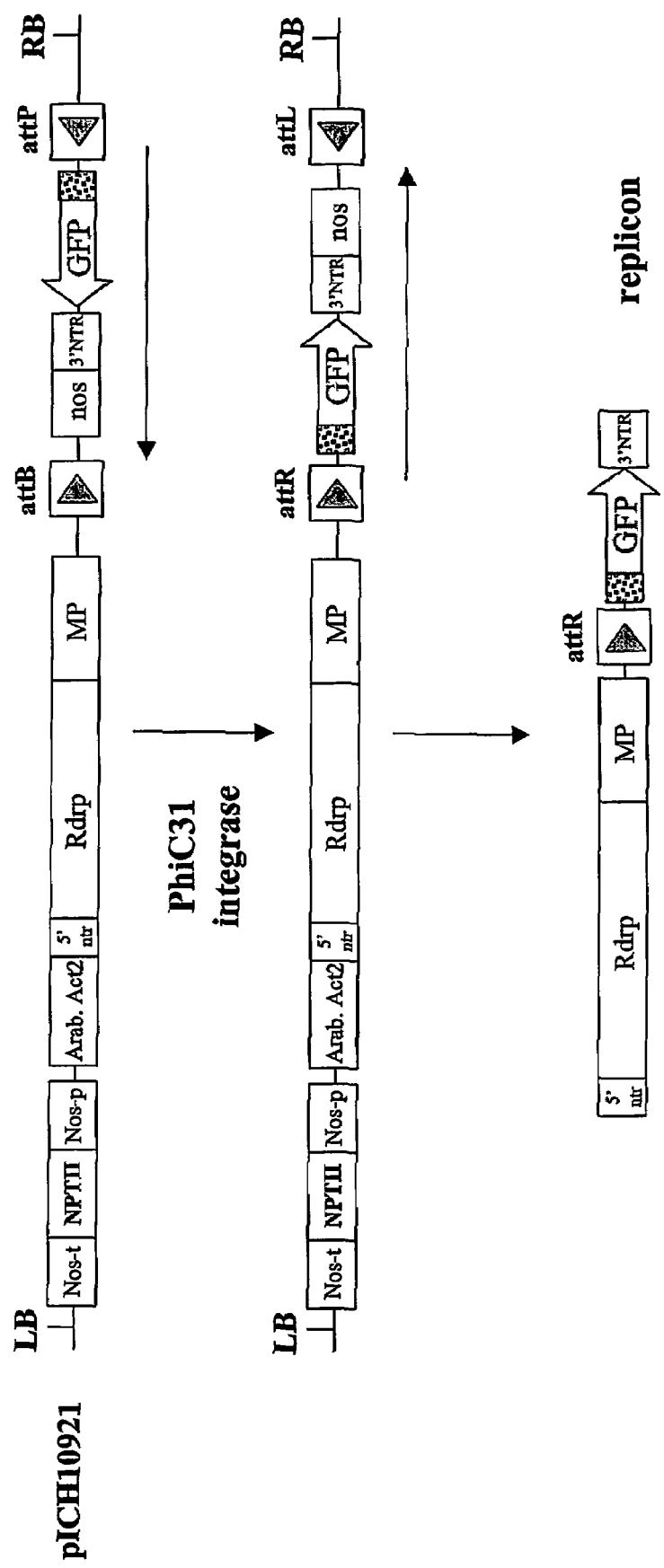
FIG. 11 depicts T-DNA region of plasmid pICH10921 and formation of an RNA replicon in the presence of integrase PhiC31 activity.

In this invention, viral replicons are preferably used that can be activated by site-specific recombination (flipping) of a certain part of the viral vector (see FIGS. 3, 9 and 11). These replicons may be based on DNA (BGMV, WDV) and RNA (TMV) viruses. It is evident from the figures that rearrangement of DNA viral vectors by site-specific recombination is sufficient to start viral DNA replication. The situation is different in the case of TMV-based vectors, as the rearrangement of DNA alone is in general not sufficient to start replication. Transcription is required in order to trigger amplification of such RNA replicons. These requirements allow to use additional controlling steps for RNA-based amplicon expression, as the constitutive promoter driving transcription (see FIG. 11) may be replaced with an inducible or a seed-specific promoter, tightening the control and providing more flexibility to the process of spatial and temporal confinement of amplification.

In order to efficiently practice said invention, analysis of many different combinations of seed-specific promoters for each type of viral replicon is preferred in order to find the best possible combination providing for the highest possible yield.

An important element of the invention is the inability of hybrid seeds to set up progeny, i.e. the seeds are preferably sterile e.g. due to their inability to develope into fertile plants. It is expected that in most cases the replication of a viral vector provides for this desired effect, thus impairing further seed development. However, if the replication of the vector providing for the product of interest is not sufficient, an additional technology may be applied in order to achieve the desired effect. In EXAMPLE 5 the use of a cytotoxic gene (barnase) assembled by intein-mediated trans-splicing in the hybrid seeds is described. The intein-fused barnase fragments are located in different parental plants and may be under control of different developmentally regulated promoters. Said fragments will be brought together upon hybridization and can form a cytotoxic product as the result of intein-mediated trans-splicing. The use of different promoters with different yet partially overlapping expression patterns allows to confine barnase activity to the required tissue in a more precise way than by using the same tissue-specific promoters to drive the expression of both barnase fragments. The shoot apical meristem-specific promoter of the *Arabidopsis* gene STM (Long et. Al., 1996, *Nature*, 379, 66-69) and the germination-specific promoter of the *Arabidopsis* gene ATHB5 (Johannesson et al., 2003, *Plant Mol. Biol.*, 51, 719-729) were used in example 5 to drive the expression of the two barnase fragments (see FIG. 15). These promoters provide for a suitable barnase activity pattern, as their activities overlap in the apical meristem of germinating seeds. This invention is not limited to the use of these two promoters as many other developmentally regulated and tissue-specific promoters can be used to practice this embodiment. Examples of useful promoters for this embodiment include the promoter of Arabidopsis HBP-1 a gene expressed in photosynteticaly active tissue (Mikami et al., 1995, *Mol. Gen. Genet*, 248, 573-582), seed-specific napin gene promoter (Ellerstrom et al., 1996, *Plant Mol. Biol.*, 32, 1019-1027), promoters of developmentally regulated rbcS genes (Manzara et al., 1991, *Plant Cell*, 3, 1305-1316), etc.

In the examples, we predominantly used *Agrobacterium*-mediated T-DNA delivery in plant cells, whereby said T-DNA contains said first and/or said second partial genetic endowment as a vector. Different methods may be used for the delivery of vectors into plant cells such as direct introduction of said vector into cells by means of microprojectile bombardment, electroporation or PEG-mediated transformation of protoplasts. *Agrobacterium*-mediated plant transformation is preferred. Thus, DNA may be transformed into plant cells by various suitable technologies such as by a Ti-plasmid vector carried by *Agrobacterium* (U.S. Pat. Nos. 5,591,616; 4,940,838; 5,464,763), particle or microprojectile bombardment (U.S. Pat. No. 5,100,792; EP 00444882B1; EP 00434616B1). In principle, other plant transformation methods can also be used e.g. microinjection (WO 09209696; WO 09400583A1; EP 175966B1), electroporation (EP00564595B1; EP00290395B1; WO 08706614A1), etc. The choice of the transformation method depends on the plant species to be transformed. For example, microprojectile bombardment may be preferred for monocots transformation, while for dicots, *Agrobacterium*-mediated transformation gives generally better results.

The present invention is preferably carried out with higher multicellular plants. Preferred plants for the use in this invention include any plant species with preference given to agronomically and horticulturally important species. Common crop plants for the use in present invention include alfalfa, barley, beans, canola, cowpeas, cotton, corn, clover, lotus, lentils, lupine, millet, oats, peas, peanuts, rice, rye, sweet clover, sunflower, sweetpea, soybean, sorghum triticale, yam beans, velvet beans, vetch, wheat, wisteria, and nut plants. The plant species preferred for practicing this invention include, but not restricted to, representatives of Gramineae, Compositeae, Solanaceae and Rosaceae.

Further preferred species for the use in this invention are plants from the following genera: *Arabidopsis, Agrostis, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonella, Triticum, Vicia, Vigna, Vitis, Zea*, and the Olyreae, the Pharoideae and many others.

Preferred are plants for which hybrid seed production systems exist. These systems are preferably used together with the present invention in order to produce a high proportion of seeds that are hybrids of said first and said second parental plants. Most preferred are corn, wheat, pennisetum, soybean, rape seed canola, tobacco, and rice.

Proteins of interest, or fragments thereof, that can be expressed, in sense or antisense orientation, using this invention include: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidin, bacterial levansucrase, *E. coli* glgA protein, MAPK4 and orthologues, nitrogen assimilation/methabolism enzyme, glutamine synthase, plant osmotin, 2S albumin, thaumatin, site-specific recombinase/integrase (FLP, Cre, R recombinase, Int, SSVI Integrase R, Integrase phiC31, or an active fragment or variant thereof), isopentenyl transferase, Sca M5 (soybean calmodulin), coleopteran type toxin or an insecticidally active fragment, ubiquitin conjugating enzyme (E2) fusion proteins, enzymes that metabolise lipids, amino acids, sugars, nucleic acids and polysaccharides, superoxide dismutase, inactive proenzyme form of a protease, plant protein toxins, traits altering fiber in fiber producing plants, Coleopteran active toxin from *Bacillus thuringiensis* (Bt2 toxin, insecticidal crystal protein (ICP), CryIC toxin, delta endotoxin, polyopeptide toxin, protoxin etc.), insect specific toxin AaIT, cellulose degrading enzymes, E1 cellulase from *Acidothermus celluloticus*, lignin modifying enzymes, cinnamoyl alcohol dehydrogenase, trehalose-6-phosphate synthase, enzymes of cytokinin metabolic pathway, HMG-CoA reductase, *E. coli* inorganic pyrophosphatase, seed storage protein, *Erwinia herbicola* lycopen synthase, ACC oxidase, pTOM36 encoded protein, phytase, ketohydrolase, acetoacetyl CoA reductase, PHB (polyhydroxybutanoate) synthase, acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, *Brassica* AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, *Umbellularia californica* C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, 6-desaturase, protein having an enzymatic activity in the peroxysomal -oxidation of fatty acids in plant cells, acyl-CoA oxidase, 3-ketoacyl-CoA thiolase, lipase, maize acetyl-CoA-carboxylase, 5-enolpyruvylshikimate-3-phosphate synthase (EPSP), phosphinothricin acetyl transferase (BAR, PAT), CP4 protein, ACC deaminase, ribozyme, protein having posttranslational cleavage site, protein fusion consisting of a DNA-binding domain of Gal4 transcriptional activator and a transcriptional activation domain, a translational fusion of oleosin protein with protein of interest capable of targeting the fusion protein into the lipid phase, DHPS gene conferring sulfonamide resistance, bacterial nitrilase, 2,4-D monooxygenase, acetolactate synthase or acetohydroxyacid synthase (ALS, AHAS), polygalacturonase, bacterial nitrilase, fusion of amino terminal hydrophobic region of a mature phosphate translocator protein residing in the inner envelope membrane of the plastid with protein of interest to be targeted into said membrane etc.

Any human or animal protein can be expressed, notably in hybrid seeds using the system of the invention. Examples of such proteins of interest include inter alia the following proteins (pharmaceutical proteins): immune response proteins (monoclonal antibodies, single chain antibodies, T cell receptors etc.), antigens, colony stimulating factors, relaxins, polypeptide hormones, cytokines and their receptors, interferons, growth factors and coagulation factors, enzymatically active lysosomal enzyme, fibrinolytic polypeptides, blood clotting factors, trypsinogen, 1-antitrypsin (AAT), as well as function-conservative proteins like fusions, mutant versions and synthetic derivatives of the above proteins.

The process of the invention may further comprise expressing a gene encoding a post-transcriptional gene silencing (PTGS) suppressor protein or a function-conservative variant or fragment thereof in a plant for suppressing PTGS of said transgenic coding sequence. Said PTGS suppressor protein gene or function-conservative variant or fragment thereof may be provided to a plant on the same vector carrying said transgenic coding sequence or on an extra vector. Said PTGS suppressor protein is preferably of viral or plant origin. Examples of PTGS suppressor proteins are potato virus X p25 protein, african cassava mosaic virus AC2 protein, rice yellow mottle virus P1 protein, tomato bushy stunt virus 19K protein, rgs CAM or a function-conservative variant or fragment of one of these proteins. Said function-conservative variant or fragment preferably has a sequence identity of 75%, preferably at least 75%, to one of the above proteins. Details on PTGS suppressor proteins and their use can be found in WO0138512.

EXAMPLES

Example 1

BGMV Vectors

Cloning of a Geminiviral Replicating Vector Carrying GFP:
pUC19 DNA was amplified with primers dnaapr7 (aac tgc agt cta gac tgg cog tog ttt tac aac) and dnaapr8 (aac tgc aga aca att gct cga ggc gta atc atg gtc a), and the amplified fragment digested with Pst1 and religated. The resulting plasmid, pICH1144, is similar to pUC19, but the polylinker has been replaced with Xho1, MfeI, and Pst1. DNA was extracted from *Phaseolus vulgaris* tissue infected by bean golden mosaic virus (BGMV) isolate DSMZ PV-0094 obtained from the German Collection of Microorganisms and Cell Cultures (DSMZ, Deutsche Sammlung von Mikroorganismen und Zelikulturen GmbH). A fragment of the genome encompassing the BGMV common region (CR; contains the BGMV origin of replication) was amplified by PCR with primers dnaapr3 (ggg aat tca cta gta aag ato tgc cgt cga ctt gga att g) and dnaapr4 (caa tgc atc atg gcg cat cac gct tag 9) and cloned as an EcoRI-NsiI fragment in pICH1144 digested with MfeI and PstI, resulting in plasmid pICH1156. The BGMV insert in pICH1156 was sequenced. Two other BGMV DNM genome fragments were amplified from BGMV infected *Phaseolus vulgaris* DNA with primers pairs dnaapr9 (aag ctg cag aag gat cct ctg gac tta cac gtg gaa tgg )/dnaapr13 (cgc tcg agg ccg tcg act tgg aat tgt c), and dnaapr5 (gaa gat ctg caa gag gag gtc agc a)/dnaapr10 (aag ctg cag atc tat ttc tat gat tcg ata acc). The sum of these fragments amounts to a complete BGMV genome without the coat protein. These fragments were digested with Xho1/Pst1 and Pst1/BglII (respectively) and cloned in a three way-ligation in pICH1156 digested with XhoI and BglIII. The resulting plasmid contains one complete BGMV DNM genome without the coat protein gene flanked by duplicated BGMV DNM common regions. Three clones were kept for testing: pICH1663, 1664 and 1667. A multicloning site containing BamHI and PstI replaces the coat protein gene. A synthetic GFP (SGFP) coding sequence was cloned as a BamHI-PstI fragment from pIC011 (Hbt promoter-Synthetic GFP coding sequence-Nos terminator in pUC18), into the BamHI-Pst1 sites of pICH1663 pICH1664 and pICH1667, resulting in plasmids pICH1693, pICH1694 and pICH1697. GFP is placed under the control of the coat protein promoter. To test for functionality of the clones pICH1693, pICH1694 and pICH1697 were bombarded in *Nicotiana benthamiana* and *Phaseolus vulgaris* excised leaves using a Biolistic Particle Delivery System 1000/HE (Biorad). GFP-expressing epidermal cells could be detected the next day in leaves of both species for all three constructs.

Cloning in Binary Vector

A binary vector containing the proreplicon part of pICH1694 was made by subcloning a XhoI-NarI fragment from pICH1694 into pICBV11 digested with Xho1 and Cla1. The resulting clone, pICH4300 (FIG. 2), contains the GFP gene under control of the BGMV coat protein promoter and the Al1/2/3 genes between duplicated CRs.

Cloning of a "Flipped" Geminiviral Provector
pICH7300 is similar to pICH4300 but several restriction enzyme sites (SalI, NcoI, MfeI, and BglII) were removed by PCR using mutated primers overlapping the restriction sites. pICH7300 was used as a starting point to make pICH1500 (FIG. 3), a clone unable to replicate due to inversion of a fragment containing part of the replicase and one of the common regions. AttP and AttB recombination sites are positioned at the extremities of the inversion to allow flipping of the inverted region by providing integrase, thereby generating a functional vector. The AttB and AttB sites are flanked by artificial intron sequences which allow splicing of the AttR sequences resulting from integrase-mediated recombination, from A11 transcripts.

Testing the Competence of Embryos for Geminiviral Replication:

pICH4300 plasmid DNA was bombarded on a series of plant tissues. Brightly fluorescent cells could be detected in *Phaseolus vulgaris* leaves, mature seed rehydrated bean cotyledon and germinating seedling, and immature embryos. Not all stages of embryo development were susceptible to geminiviral replication as assayed by GFP fluorescence. Small white embryos with cotyledons up to 4 to 5 mm in length did not exhibit any GFP-expressing cell. In contrast, bigger cotyledons with a more greenish color were very competent for geminiviral replication.

Other species were also susceptible to geminiviral replication, a least in leaves, including *Nicotiana tabacum, Nicotiana benthamiana, Arabidopsis thaliana, Orychophragmus violaceus* and Mung bean.

Figure 6:
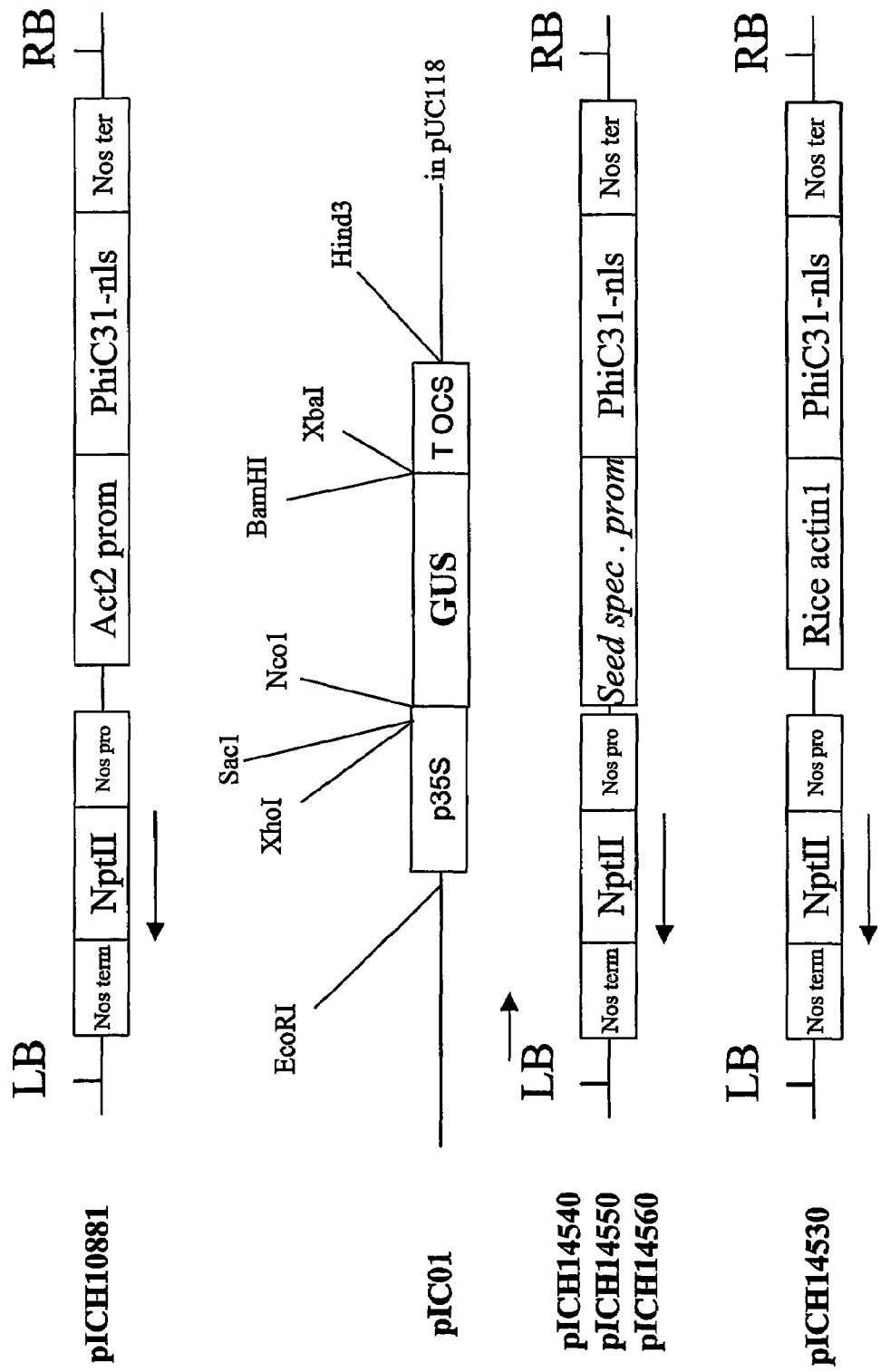
FIG. 6 shows schemes of the T-DNA regions of constructs pICH10881, pICH14540, pICH14550, pICH14560, pICH14530 and construct pIC01.

Cloning of PhiC31 Integrase Clones pICP1010 is a binary vector containing the *Streptomyces* Phage C31 integrase (from David Ow, Plant Gene Expression Center, US Department of Agriculture—Agricultural Research Service, Albany, Calif. 94710, USA) fused to the *Arabidopsis* Actin 2 promoter (a 1344 nt fragment containing the promoter, 1st exon, 1st intron and 10 nucleotides of the 1st exon of the actin 2 gene). To increase integrase transport to the nucleus, a nuclear localization signal from the SV40 T-antigen (Pro-Lys-Lys-Lys-Arg-Lys-Val, Andreas et al., 2002, *Nucleic Acids Res.*, 30, 2299-2306) was fused to the C-terminal end of the PhiC31 integrase. The NLS sequence was added to integrase sequences by PCR amplification from pICP1010 using primer c31pr1 (gca cgc cga agg cga cga ag) and a PCR primer containing an extension containing the NLS sequence (31nls1: gga tcc taa acc ttc ctc ttc ttc tta ggc gcc gct acg tct tcc gtg), and subcloning as a BspEI -BamHI fragment in pICP1010, resulting in plasmid pICH10881 (FIG. 6). To easily subclone different promoters, the integrase and the Nos terminator were subcloned from pICH10881 as a Pst1 Apa1 fragment in pICH13901, an Icon Genetics binary vector containing a Nos promoter-NptII coding sequence-Nos terminator selection cassette and a polylinker Kpn1-Xho1-Pst1-Apa1-Hind3, resulting in plasmid pICH13901 (not shown). Several promoters were amplified with gene-specific primers from genomic DNA of the appropriate species and cloned as a Kpn1/Xho1 fragment in pICH13901. Said promoters were also subcloned as EcoR1/Xho1 fragments into the pIC01 (FIG. 6) and tested for their activity as fusions with GUS reporter gene using microprojectile bombardment of developing seeds (not shown).

For driving the expression of integrase PhC31, we have chosen several monocot and dicot seed-specific promoters including promoter of USP gene from *Vicia faba* (Fiedler et al, 1993, *Plant Mol. Biol.* 22, 669-679), promoter of AtEm6 gene (Vicient et al., 2000, *J. Exp. Botany*, 51, 1211-1220), promoter of maize rab17 gene (Busk et al., 1997, *Plant J.*, 11, 1285-1295) as well as constitutive promoters of *arabidopsis* actin 2 and rice actin 1 genes (constructs pICH14540, pICH14550, pICH14560, pICH10881 and pICH14530 respectively, see FIG. 6).

Stable Transformation and Hybridization Experiments

The *Nicotiana benthamiana* leaf discs were transformed with constructs pICH1500, pICH4550 and pICH4540 (integrase), generating transformants independent for each construct. Ten pICH1500 transformants were crossed with at least 5 transformants of each integrase construct. Immature developing seeds were dissected and GFP fluorescence observed under blue light with a microscope.

Example 2

WDV Vectors

DNA was extracted from a wheat dwarf virus (WDV)-infected wheat leaf sample obtained from the German Collection of Microorganisms and Cell Cultures (DSMZ, Deutsche Sammlung von Mikroorganismen und Zellkulturen GmbH). A complete genome of the WDV (ca. 2.8 kb) was PCR-amplified using primers directed in opposite orientations and overlapping the unique EcoRI site of the genome:

```
FwdvE1        aGAATTCacaccgatgggctc

RewdvE1       tGAATTCtgcacactcccacg
```

The amplified fragment was cloned into the pGEM-T Vector (Promega). Two clones were sequenced. BLAST analysis revealed that the amplified sequence differed significantly from the four completely sequenced WDV strains (GEWDVX)(, WDVGNS, WDW311031, NC_003326) present in the EMBL/Genbank databases, but matches closely a partially sequenced (1.2 kb) virus isolate from Hungary (AJ311038; *Arch. Virol.* 147 (1): 205-216, 2002).

Based on the sequence data obtained, two primers were designed (ttC CAT Gga gtt acc tcg gg agt cct tgt tg and ttG CAT GCG GCC Gca aaa tag tat ttt att cat ctc atg tc) for amplification of a complete genome with the exception of the coat protein gene. PCR was performed from the infected leaf DNA described above.

Figure 13:
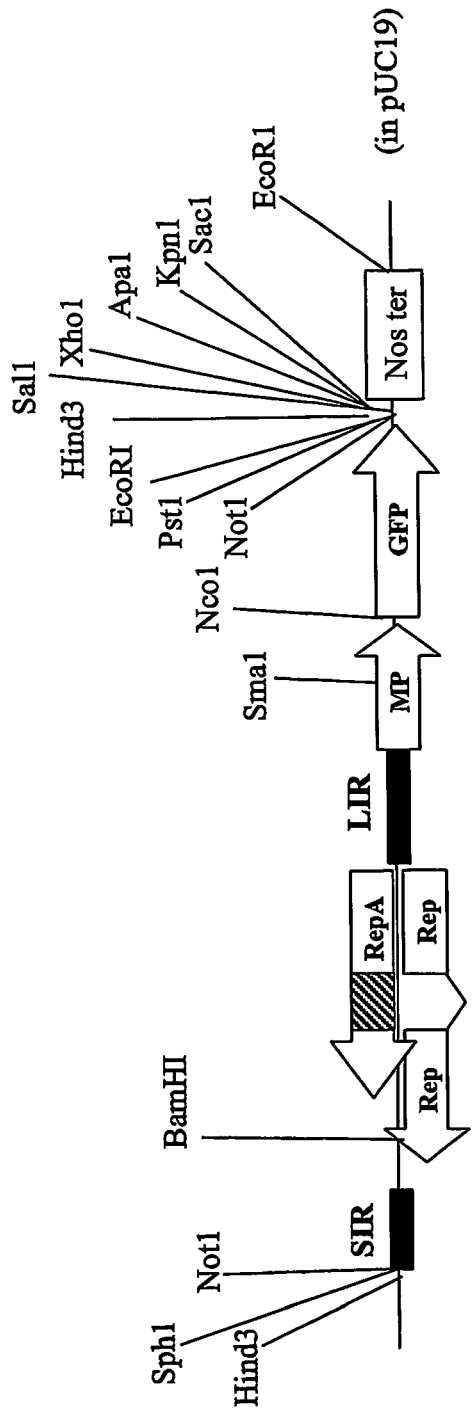
FIG. 13 depicts a schematic representation of the construct pICH10680.

The amplified PCR product was cloned as a SphI-NcoI fragment into pUC19 vector containing mutant version of GFP (S65TGFP) digested with SphI and NcoI. The resulting clone pICH10680 contains a single WDV genome with GFP replacing CP (FIG. 13).

A complete genome with duplicated LIR was cloned in binary vector in two steps. First, a BamHI-ApaI fragment from pICH10680 was subcloned into Binary vector digested with BglII and ApaI. This intermediate clone, containing a partial WDV genome with GFP instead of CP, digested with PspoMI and PciI (blunted with Klenow), was used in a second step of cloning a SmaI-NotI fragment from pICH10680. The resulting clone, pICH10830 (FIG. 7), contains a complete WDV genome with GFP replacing CP, and is flanked by duplicated LIR, allowing exision and amplification of the WDV-GFP replicon.

Testing Competence of Embryos for Geminiviral Replication:

pICH10830 was bombarded into developing embryos of wheat and maize. Cells expressing strong GFP fluorescence were observed in the embryos, but could also be detected in endosperm (FIG. 8).

Cloning of a "Flipped" WDV Provector

With the same strategy as decribed for BGMV vectors, a "flipped" WDV vector was made, pICH14520 (FIG. 9). This clone becomes capable to initiate replication only after flipping by exposure to PhiC31 integrase. To test the functionality of this clone it was bombarded in maize embryo alone or with integrase clones pICH14530 or pICH14560. GFP fluorescent cells could be detected only when pICH14520 was cobombarded with integrase.

Stable Transformation and Hybridization Experiments pICH14520 and the integrase clone were transformed in maize.

Selected transformants from both constructs were crossed together in both directions and immature seeds dissected at diverse developmental stages and observed under blue light using a microscope or a handheld UV lamp.

Example 3

CR-TMV Vectors

Figure 10:
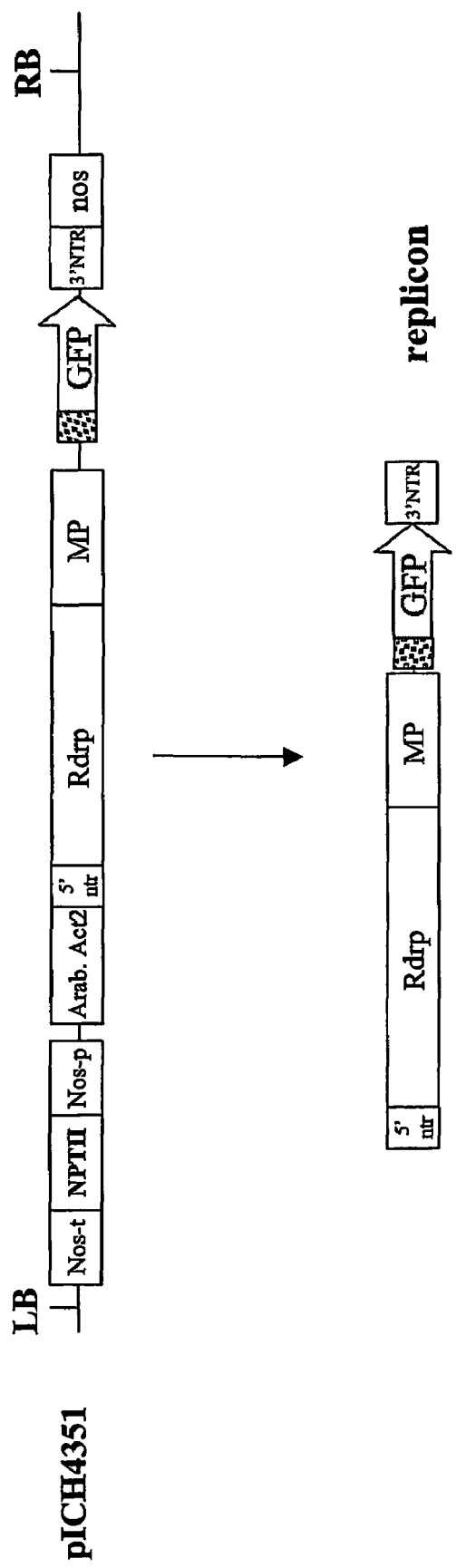
FIG. 10 depicts the T-DNA region of plasmid pICH4351 and formation of an RNA replicon. The grey-dotted element next to GFP indicates an IRES (internal ribosome entry site) element.

Cloning of a cr-TMV Replicating Vector Carrying GFP:

pICH4351 (FIG. 10) is a viral vector based on cr-TMV, a crucifer-infecting tobamovirus (Dorokhov et al., 1994, *FEBS Letters*, 350, 5-8). pICH4351 contains the 5' untranslated sequences of Cr-TMV followed by RdRp and MP (nucleotides 1 to 5629 from Genbank accession Z29370, the last 16 aminoacids of MP were truncated without a loss of MP function, and a T at position 5605 in Z29370 was mutated to a C), fused to the *Arabidopsis* Actin 2 promoter (a 787 nt fragment 5' of the transcription start, Genbank accession U41998, An et al., 1996, *Plant J.*, 10, 107-121). The MP is followed by a LoxP site. This site has no functional significance for the use of this construct and is present because it was also present in the plasmids used to construct it. The LoxP is followed by an IRES sequence from cr-TMV (nucleotides 4804 to 4873 from Genbank accession Z29370) and by the GFP ORF. Ires was cloned in this position as a translational enhancer to increase GFP expression. GFP is followed by cr-TMV 3' untranslated sequences (nucleotides 6083 to 6312 from Genbank accession Z29370) followed by the *Agrobacterium* Nos terminator. This construct is cloned in an Icon Genetics binary vector pICBV10, carrying a cassette for Kanamycin selection in plants (Nos promoter-NPTII coding sequences-Nos terminator). In this construct, GFP is expressed from the CP subgenomic promoter located at the end of the MP. After delivery to the nucleus by bombardment or agroinfiltration, a primary transcript made in the nucleus from the Actin2 promoter is exported to the cytoplasm where replication takes place.

Cloning of a "Flipped" cr-TMV Provector pICH10921 is a viral pro-vector made from pICH4351 (FIG. 11). It differs from pICH4351 by the fact that a DNA fragment extending from the Ires to the Nos terminator was flipped in inverse orientation to render the construct incapable of replication. To allow flipping of this fragment, a PhiC31 AttP site (gta gtg ccc caa ctg ggg taa cct ttg agt tct ctc agt tgg ggg cgt aga) and AttB site (tcg aag ccg cgg tgc ggg tgc cag ggc gtg ccc ttg ggc tcc ccg ggc gcg tac tcc acc tca ccc atc) are positioned at the extremities of the inversion.

To test whether flipping of the inverted part leads to a functional vector, pICH10921 was transformed into *agrobacterium* strain GV3101 and used for agroinfiltration of *Nicotiana benthamiana* leaves. No GFP spots were detected when pICH10921 was infiltrated alone, but numerous GFP replication foci could be seen when pICH10921 was coinfiltrated with agrobacteria transformed with pICH10881 (containing an integrase expressing vector).

Stable Transformation and Hybridization Experiments pICH10921, pICH10881, pICH14540 and pICH14550 were transformed separately in *Nicotiana benthamiana* by leaf disc transformation using 50 mg/L of Kanamycin for selection of transformants (Horsh et al., 1985, *Science*, 227, 1229-1231). Selected transformants from both constructs were crossed together in both direction and immature seeds dissected and observed under blue light using a microscope. GFP expression was detected in hybrid seeds.

Example 4

Generation of Transgenic *Zea mays* Plants

Figure 12:
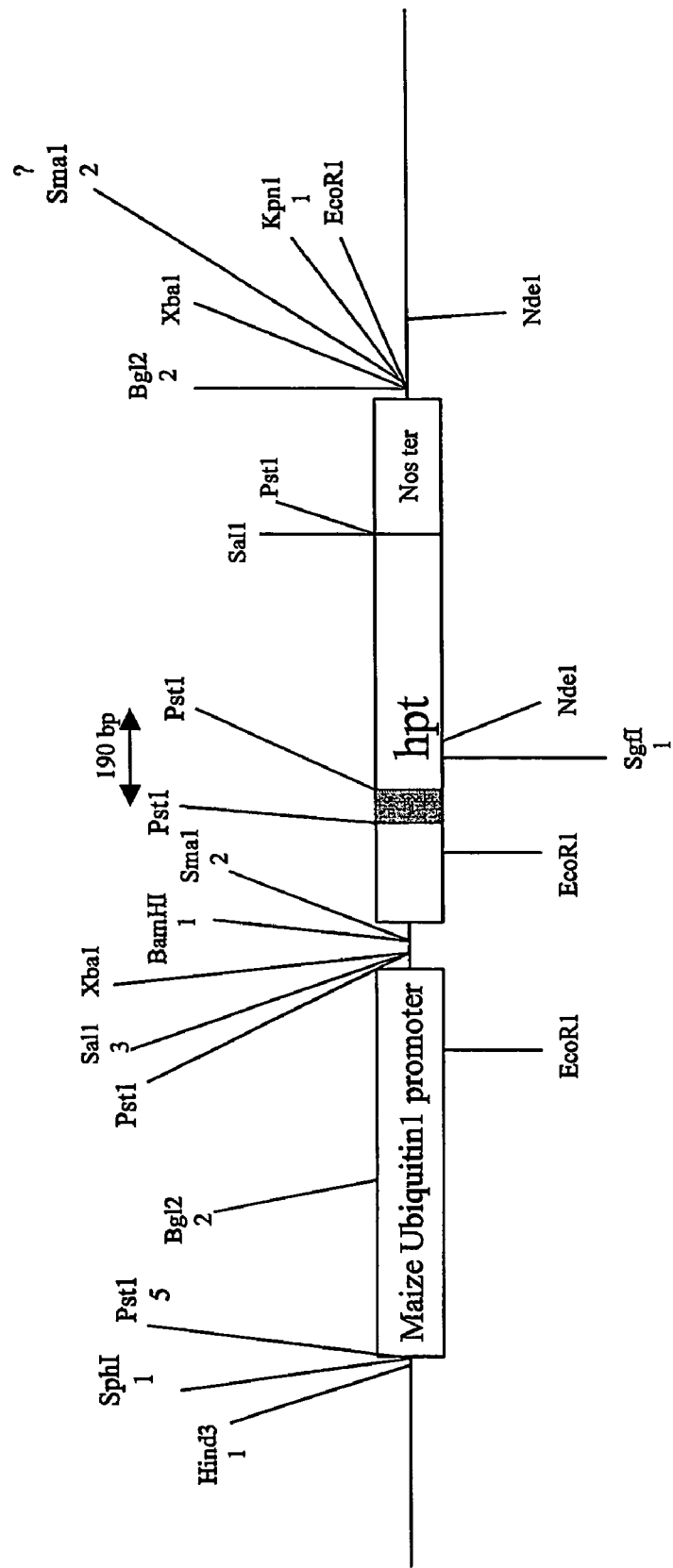
FIG. 12 depicts a schematic representations of plasmid pICH1600.

A hygromycin phosphotransferase gene (HPT) under control of the maize ubiquitin promoter was used as selectable marker for monocot transformation (FIG. 12). Hygromycin B as selection agent was applied at concentrations 25-100 mg/l.

The following method was used for generating transgenic *Zea mays* plants:

Callus cultures were induced from mature and immature embryos of the lines A188, Hill etc.

The culture media were based on Chu (N6) salts and vitamins (Chu et al., *Scientia Sinica*, 18(5):659-68,1975).

Callus induction and propagation medium was supplemented with 30 g/l sucrose, 600 mg/l L-proline, 2.0 mg/l of 2,4-D and 0.3% gelrite.

Pre-regeneration medium was not used. Regeneration medium contained N6 salts and vitamins, 30 g/l sucrose, 2 mg/l Zeatin and 0.05 mg/l 2,4D. Silver thiosulfate was included in the regeneration medium at concentrations 0.01-0.06 mM.

Microprojectile Bombardment

Microprojectile bombardment was performed utilizing the Biolistic PDS-1000/He Particle Delivery System (Bio-Rad). The cells were bombarded at 900-1100 psi, at 15 mm distance from a macrocarrier launch point to the stopping screen and 60 mm distance from the stopping screen to a target tissue. The distance between the rupture disk and the launch point of the macrocarrier was 12 mm. The cells were bombarded after 4 hours of osmotic pretreatment A DNA-gold coating according to the original Bio-Rad's protocol (Sanford et al., 1993, In: Methods in Enzymology, ed. R. Wu, 217, 483-509) was done as follows: 25 µl of gold powder (0.6, 1.0 mm) in 50% glycerol (60 mg/ml) was mixed with 5 µl of plasmid DNA at 0.2 µg/µl, 25 µl $CaCl_2$ (2.5 M) and 10 µl of 0.1 M spermidine. The mixture was vortexed for 2 min followed by incubation for 30 min at room temperature, centrifugation (2000 rpm, 1 min), washing by 70% and 99.5% ethanol. Finally, the pellet was resuspended in 30 µl of 99.5% ethanol (6 µl/shot).

A new DNA-gold coating procedure (PEG/Mg) was performed as follows: 25 µl of gold suspension (60 mg/ml in 50% glycerol) was mixed with 5 µl of plasmid DNA in an Eppendorf tube and supplemented subsequently by 30 µl of 40% PEG in 1.0 M $MgCl_2$. The mixture was vortexed for 2 min and than incubated for 30 min at room temperature without mixing. After centrifugation (2000 rpm, 1 min) the pellet was washed twice with 1 ml of 70% ethanol, once by 1 ml of 99.5% ethanol and dispersed finally in 30 µl of 99.5% ethanol. Aliquots (6 µl) of DNA-gold suspension in ethanol were loaded onto macrocarrier disks and allowed to dry up for 5-10 min.

Plasmid DNA Preparation

Plasmids were transformed into *E. coli* strain DH10B, maxi preps were grown in LB medium and DNA was purified using the Qiagen kit.

Selection

For stable transformation experiments, the filters with the treated cells were transferred onto solid MS2 medium with the appropriate filter-sterilized selective agent (150 mg/L hygromycin B (Duchefa). 3% sucrose and kept in the dark. Every seven days the material was transferred to fresh selection media. The plates were kept in the dark and after approximately 6 weeks the plant material was transferred to the Petri plates with regeneration medium and appropriate selection agent (150 mg/L hygromycin B). The plates were incubated at high light intensity, 16 hours day length.

Example 5

The Barnase-based Sytem for Controlling the Hybrid Seed Development

The barnase gene was split using the *Synechocystis* sp. PCC6803 DnaB intein. DNA fragments for the N and C-terminal parts of Barnase flanked by appropriate restriction sites were chemically synthesized by a commercial DNA-synthesis company.

The sequence of the N terminal end is:

5' gcaatcgatg gcacaggtta tcaacacgtt tgacgggggtt gcggattatc ttcagacata tcataagcta cctgataatt acattacaaa atcagaagca caagccctcg gctgggacgt ccgc 3'

The sequence of the C terminal end is:

5' cgccatgggg tggcatcaaa agggaaccttt gcagacgtcg ctccgggg gaa aagcatcggc ggagacatct tctcaaacag ggaaggcaaa ctccccgggca aaagcggacg aacatggcgt gaagcggata ttaactatac atcaggcttc agaaattcag accggattct ttactcaagc gactggctga tttacaaaac aacgaccat tatcagacct ttacaaaaat cagataagga tccgc 3'.

Figure 14:
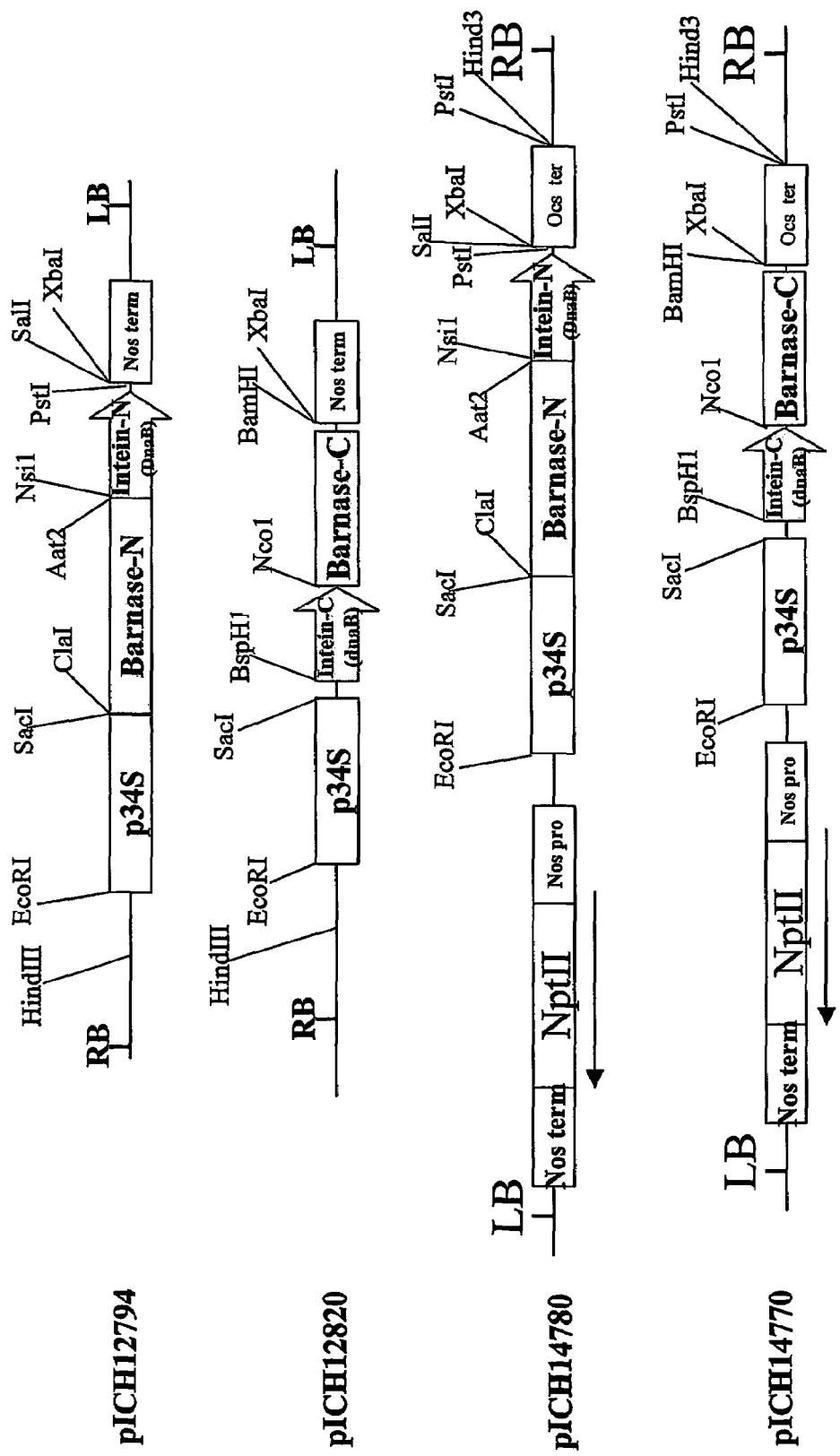
FIG. 14 depicts a schematic representation of the constructs pICH12784, pICH12820, pICH14780 and pICH14770.

The N terminal end of Barnase was fused to the N-part of the DnaB intein. The DnaB intein-N fragment was amplified from *Synechocystis* DNA using primers DnaBintNpr1 (5' gtAAGCTTGA CGTcagagag agtggatgca tcagtggaga tag 3') and DnaBintNpr2 (5' caCTGCAGct ataattgtaa agaggagctt tctag 3'). The Barnase fragment (a ClaI AatII fragment) and the intein fragment (a AatII PstI fragment) were cloned in an Icon Genetics binary vector resulting in clone pICH12794 (FIG. 14).

The C terminal end of Barnase was fused to the C part of the DnaB intein. The DnaB intein-C fragment was amplified from *Synechocystis* DNA using primers dnaBintCpr1 (gt GAG CTC G ATC GAT TCA TGA gcc cag aaa tag aaa agt tgt ctc) and dnaBintCpr2 (tc MG CTT CCA TGG tct tgc tct tca ctg tta tgg aca atg atg tca t). The intein fragment (a $Sac_1$ NcoI fragment) and the Barnase fragment (a NcoI BamHI fragment) were cloned in an Icon Genetics binary vector, resulting in clone pICH12820 (FIG. 14).

Functionality of the N and C terminal Barnase-intein fusion clones was tested by agroinfiltration of *Nicotiana benthamiana* leaves. As expected, leaf area coinfiltrated with both constructs became necrotic while areas infiltrated with either construct alone remained healthy.

PICH12794 and pICH12820 were subcloned in pICBV16, an Icon Genetics binary vector with a NptII casette for kanamycin selection of plant transformants. The resulting plasmids are pICH14780 and pICH14770 (FIG. 14).

Figure 15:
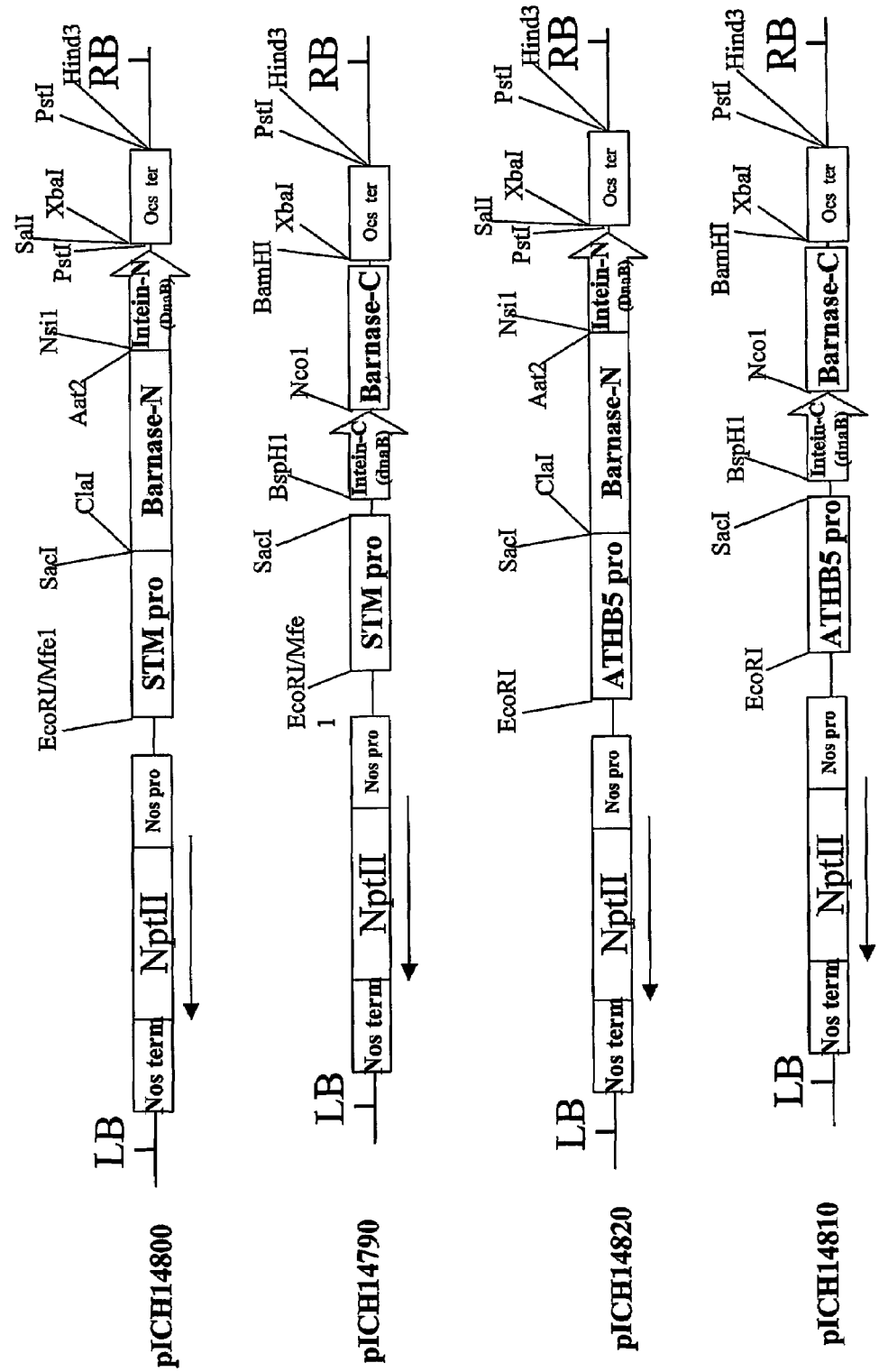
FIG. 15 depicts a schematic representation of the constructs pICH14800, pICH14790, pICH14820 and pICH14810.

The shoot apical meristem-specific promoter of the *Arabidopsis* gene STM (Long et. Al., 1996, *Nature,* 379, 66-69) was amplified from *Arabidopsis* genomic DNA using primers STMfwd (cg caattg gtggcaagaggtctaccatct) and STMrev (gc gagctcttctctttctctcactagtatt) and subcloned as an Mfe1 Sac1 fragment in pICH14770 and pICH14780 (digested with EcoRI SacI), resulting in plasmids pICH14790 and pICH14800 (FIG. 15). The promoter region was sequenced in both plasmids. pICH14790 and pICH14800 consist of the C and N-terminal Barnase-intein fusions under control of the STM promoter.

The germination-specific promoter of the *Arabidopsis* gene ATHB5 (Johannesson et al., 2003, *Plant Mol. Biol.,* 51, 719-729) was amplified from Arabidopsis genomic DNA using primers ATHB5Fwd (cg gaatt ccagctcatcaaccaaactctgt) and ATHB5rev (gc gagctctttgctctgtgtctagactatcc) and subcloned as an EcoRI Sac1 fragment in pICH14770 resulting in plasmid pICH14810 (FIG. 15). The amplified fragment was sequenced from pICH14810 and subcloned as a EcoRI Sac1 fragment in pICH14780 resulting in pICH14820 (FIG. 15). pICH14810 and pICH14820 consists of the 5' and 3' Barnase-intein fusions under control of a germination-specific promoter.

All 4 plasmids were introduced in *Agrobacterium* strain GV3101 and used for *Arabidopsis* transformation. All transgenic plants were phenotypically normal. Transgenic plants were crossed with the plants containing the complementary barnase construct, with the same promoter or a different promoter. Use of different promoters allows to restrict activity of Barnase to the area of overlap of the promoters used. F1 seeds were harvested after dessication and sown. They germinated but were arrested due to a lack of a meristem.

The invention claimed is:

1. A process of producing a protein of interest in an F1 seed, said process comprising:
   (a) hybridizing a first and a second transgenic parental plant, whereby an F1 seed is produced, wherein said first transgenic parental plant has integrated in its genome a precursor of a replicating DNA as a first partial genetic endowment, said replicating DNA encoding said protein of interest and comprising a plant geminiviral origin of replication and a nucleic acid sequence encoding a plant geminiviral replicase, said second transgenic parental plant encodes, as a second partial genetic endowment, a site-specific recombinase, integrase or flippase for generating said replicating DNA by rearranging the precursor of said replicating DNA by site-specific recombination, and said hybridizating generates in said F1 seed said replicating DNA by combining in said F1 seed said first and said second partial genetic endowments of said first and said second transgenic parental plant; and
   (b) isolating from said F1 seed or a seedling thereof,
       (i) said protein of interest, or
       (ii) if said protein of interest is an enzyme, a chemical compound the synthesis of which said enzyme is involved in.

2. A process of producing a protein of interest in an F1 seed, said process comprising:
   (a) hybridizing a first and a second transgenic parental plant, whereby an F1 seed is produced, wherein said first transgenic parental plant has integrated in its genome a precursor of a replicating DNA as a first partial genetic endowment, said replicating DNA encoding said protein of interest and comprising a plant geminiviral origin of replication and a nucleic acid sequence encoding a plant geminiviral replicase, said second transgenic parental plant encodes, as a second partial genetic endowment, a site-specific recombinase, integrase or flippase for generating said replicating DNA by rearranging the precursor of said replicating DNA by site-specific recombination, and said hybridizating generates in said F1 seed said replicating DNA by combining in said F1 seed said first and said second partial genetic endowments of said first and said second transgenic parental plant, whereby said protein of interest is not expressed in said first or said second parental plant; and
   (b) isolating from said F1 seed or a seedling thereof,
       (i) said protein of interest, or
       (ii) if said protein of interest is an enzyme, a chemical compound the synthesis of which said enzyme is involved in.

3. The process according to claim 1, wherein said replicating DNA is generated by combining in said F1 seed a site-specific recombinase from a first parental plant and a precursor of said replicating DNA from a second parental plant.

4. The process according to claim 1, wherein said replicating DNA is an autonomous plasmid.

5. The process according to claim 1, wherein transcription of RNA or proteins necessary for formation of said replicating DNA is controlled by a constitutive promoter, seed-specific promoter, or chemically regulated promoter.

6. The process according to claim 1, wherein said protein of interest accumulates in the developing embryo, in the endosperm, in cotyledons or in germinating seeds.

7. The process according to claim 1, wherein said plants are monocots or dicots.

8. The process according to claim 1, wherein the female parental plant of said hybridization is male-sterile.

9. The process according to claim 1, wherein said protein of interest is encoded in the partial genetic endowment provided by the female parental plant of said hybridization.

10. The process according to claim 1, wherein production of said protein of interest in said seed is triggered by said generation of said genetic endowment.

* * * * *